(12) United States Patent
Alfa

(10) Patent No.: US 6,447,990 B1
(45) Date of Patent: Sep. 10, 2002

(54) ARTIFICIAL TEST SOIL

(75) Inventor: Michelle J. Alfa, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 09/762,288

(22) PCT Filed: Aug. 9, 1999

(86) PCT No.: PCT/CA99/00727
§ 371 (c)(1),
(2), (4) Date: May 25, 2001

(87) PCT Pub. No.: WO00/09743
PCT Pub. Date: Feb. 24, 2000

Related U.S. Application Data

(60) Provisional application No. 60/095,932, filed on Aug. 10, 1998.

(51) Int. Cl.⁷ .................................................. C12Q 1/00
(52) U.S. Cl. ........................... 435/4; 510/114; 510/226; 510/305
(58) Field of Search .................. 435/4; 134/2; 510/114, 510/226, 305

(56) References Cited

FOREIGN PATENT DOCUMENTS

| EP | 0 884 115 A2 | 12/1998 |
| EP | 0 884 115 A | * 12/1998 |
| WO | WO 97/27482 | 7/1997 |
| WO | WO 98/40736 | 9/1998 |

* cited by examiner

*Primary Examiner*—Ralph Gitomer
(74) *Attorney, Agent, or Firm*—Bereskin & Parr; Micheline Gravelle

(57) ABSTRACT

An artificial test soil (ATS) for "simulated-use" testing and cleaning validation studies of medical devices (including narrow lumened flexible endoscopes and other difficult to clean medical devices) is described. In addition, a cleaning validation test kit is described for users of medical devices to determine if adequate cleaning/rinsing has been performed on the medical device. The ATS formulations are based on the "worst-case" types and amounts of physiological soil components present in material recovered from patient-used flexible narrow-lumened endoscopes used for colonoscopy, bronchoscopy and duodenoscopy, but is applicable to a wide range of medical devices that might encounter similar types of soil.

21 Claims, 7 Drawing Sheets

Benchmark Data for Hemoglobin from Patient-used Colonoscopes

Benchmark Data for Endotoxin from Patient-used Colonoscopes

Median pre-cleaning: 10.4 EU/cm2

Benchmark Data for Bioburden from Patient-used Colonoscopes

Benchmark Data for Bilirubin from Patient-used Colonoscopes

Benchmark Data for Sodium ion from Patient-used Bronchoscopes

ARTIFICIAL TEST SOIL

This application is a national phase entry under 35 USC 371 of PCT/CA99/00727 filed Aug. 9, 1999 which claims priority from U.S. provisional application serial No. 60/095, 932. filed Aug. 10, 1998 (now abandoned), which is incorporated herein by reference.

FIELD OF THE INVENTION

The present invention relates to an artificial test soil for simulated use testing and cleaning validation studies of medical devices.

BACKGROUND OF THE INVENTION

Proper reprocessing, which includes cleaning and/or disinfection/sterilization of medical devices is critical to ensure patient safety. The Association for the Advancement of Medical Instrumentation Technical Information Report (AAMI TIR #12, 1994), indicates that cleaning procedures and simulated use testing should be based on the type and quantity of contamination expected to be on the device after patient-use. Furthermore, the AAMI TIR goes on to indicate that "the soil selected should be that which most closely simulates the contamination and actual clinical use". In a draft guidance document (Nov. 5, 1998) produced by the Infection Control Devices Branch of the Food and Drug Administration (FDA), manufacturers are instructed to use "worst case conditions" in their simulated-use testing. In addition, manufacturers are recommended to use an organic challenge "representative of the types of soil to which devices are exposed during clinical use". The guidance document also recommends " . . . that the bioburden challenge (organic and microbial) to the cleaning and/or disinfection process of the washer and washer-disinfectors be determined from clinically used devices." A draft guidance document for liquid chemical sterilants and high level disinfectants prepared by the FDA (Dec. 18, 1997) also provides simulated-use guidelines that have similar "worst-case" guidelines requiring an organic challenge "representative of the type of organic load to which the device is exposed during actual use such as serum, blood, secretions etc." Despite these recommendations, there have been no publications that provide experimental data regarding the type and composition of soil (other than for viable bioburden determinations) that would be expected from medical devices.

Many test soils have been described and published for use in simulated-use testing, cleaning, high level disinfection, and sterilization validation studies. These published test soils include; Huckers soil, Edinburgh soil, various concentrations of whole blood, fibrin, a mixture of serum, dry milk powder, blood plus saline, and various concentrations of serum (AAMI TIR #12; 1994, Jacobs et al 1998, FDA December 1997, Verjat et al 1999). The wide range of test soils utilized by manufacturers and independent research groups have made it difficult to compare evaluations of the efficacy of sterilizers, and washer/disinfectors for reprocessing of medical devices. Likewise evaluations of cleaners or disinfectants are difficult to compare when the inorganic/organic test soil challenge is different. It would be a great value to have a standardized test soil that could be utilized by manufacturers as it would allow appropriate comparisons to be made between various studies.

Previous formulations of test soils including; Hucker's soil, Edinburgh soil, various blood concentrations, fibrin, and various serum concentrations were not based on experimental data obtained from patient-used medical devices. Rather, they were based on common sense determinations. An example would be Hucker's soil (AAMI TIR # 12), which contains lard, peanut butter, butter, flour, evaporated milk, egg yolk, ink, saline and dehydrated blood which was meant to simulate fecal material. The test soils comprised of various serum or blood concentrations were used since medical devices employed for surgery, or exposed to mucosal surfaces would be expected to be come in contact with such body substances. What is not known is the concentration of the various components such as protein, carbohydrate etc of such secretions that would be present.

The FDA recommendations and current guidelines by AAMI have recognized that "simulated-use" testing should include a representative inorganic/organic challenge. Otherwise testing by manufacturer's will not mimic actual in-use conditions and could lead to approval of reprocessing methods that put patients at risk simply because the pre-testing was not challenging enough to identify potential problems. At the same time too harsh an inorganic/organic challenge is of little value, as all "simulated-use" testing would fail and potentially safe devices/processes would be unfairly prevented from being used.

The test soil formulations that have been published to date are not standardized and therefore, comparison of different studies is difficult as different test soil formulations were used. Because there has been no published data indicating what concentrations of the various soil parameters are present in secretions that patient-used medical devices are exposed to, there has been no basis for reaching a consensus regarding standardization of a test soil for "simulated-use" testing. The test soils that have been published to date have inappropriately high amounts of components such as hemoglobin or protein, yet lack other components such as bilirubin and endotoxin as shown herein. In addition, Jacobs et al (1998) have suggested that a ratio of protein to inorganic salts of about 10:1 is " . . . not representative of the type of soils commonly found on surgical devices." This is shown herein not to be correct.

Currently there are no commercially available test kits that allow users to validate that adequate cleaning has been performed. The AAMI TIR #12 recommends "Any test procedures that can be easily replicated in a health care facility and that can help user recognize whether or not cleaning was effective for all device surfaces should also be provided. Such tests are particularly important for devices with components that cannot be readily inspected for cleanliness (e.g. spring hinges, lumens, porous materials, crevices)." Despite this recommendation, the availability of such tests is currently very limited. Cleaning validation is an integral part of an effective quality assurance program and staff competency validation. Despite recommendations by guidelines that indicate that Quality Assurance and staff training are critical parameters (Martin 1994, DiMarino et al 1996) for reprocessing of medical devices, no published or commercial methods exist for users to address these needs. There are a few published descriptions of cleaning validation tests based on residual protein (Kruger 1997, Verjat et al 1999, Roth et al 1999), however, no validation using patient-used devices has been included. In other words, the benchmark of what is an acceptable level of the test parameter was not determined experimentally and the cutoffs chosen in these reports were based on limits of detection of the test rather than actual in-use benchmark determinations. The cleaning validation method described by Roth et al (1999) does have benchmark data, but is based on radioactive tracer soil and as such is attuned to manufacturers and is not a test that could be adapted by users.

In view of the foregoing, there is a need in the art to provide test soil formulations that can effectively simulate soil levels from an actual clinical setting. There is also a need for cleaning validation kits to enable users to confirm that they have adequately cleaned a medical device.

SUMMARY OF THE INVENTION

The present invention provides an artificial test soil for simulated use testing and cleaning validation studies of medical devices. The artificial test soil (ATS) comprises: base medium, serum, blood and endotoxin. The artificial test soil may optionally contain bilirubin and/or mucin or carbohydrate.

In a preferred embodiment, the artificial test soil comprises: base medium, up to 20% v/v serum; up to 10% v/v blood; and up to 2,000,000 EU/ml endotoxin. If present, the bilirubin will be in the amount of about 1,000 nmoles/ml and the mucin or carbohydrate will be in the amount up to 10,000 µg/ml.

The artificial test soil (ATS) can be used in many applications including (a) use by manufacturers to test equipment and cleaning and/or sterilization/disinfection compositions; (b) use by hospitals and other institutions to ensure adequacy of reprocessing; and (c) use to train staff in proper reprocessing procedures. In all these applications the ATS is used to evaluate the efficiency of a reprocessing method on a device. Accordingly, the present invention provides a method of evaluating a reprocessing method on a device comprising:

(a) applying an artificial test soil (ATS) comprising base medium, serum, blood and endotoxin to the device;

(b) subjecting the device to the reprocessing method to be evaluated; and (c) determining the presence or absence of at least one contaminant on the device.

The ATS can also be used to evaluate the efficiency of a reprocessing method on the killing of microorganism(s).

Accordingly, the present invention provides a method of determining whether a reprocessing method can kill a microorganism on a device comprising:

(a) inoculating an artificial test soil (ATS) with a microorganism wherein the ATS comprises base medium, serum, blood and endotoxin;

(b) applying the inoculated ATS to the device;

(c) subjecting the device to the reprocessing method to be evaluated; and (d) determining the presence or absence of the microorganism on the device.

The present invention also relates to a cleaning validation test kit comprising the artificial test soil of the invention and an indicator to determine if the contamination has been adequately removed from the medical device.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

1. Artificial Test Soil

Figure 1:
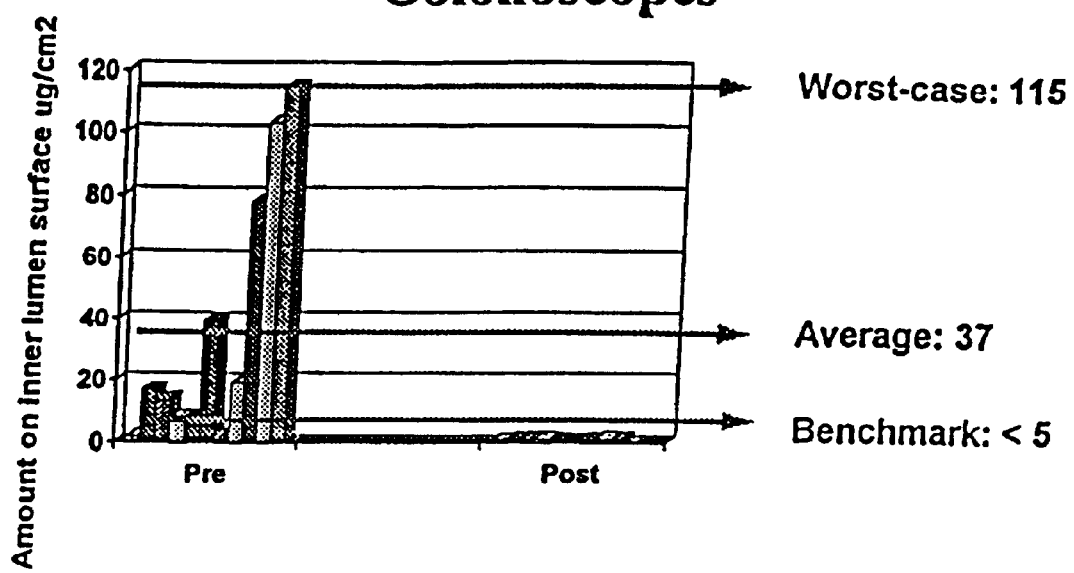
FIG. 1 is a bar graph showing the amount of protein on colonoscopes.

The present invention provides an artificial test soil for simulated use testing and cleaning validation studies of medical devices. The artificial test soil comprises: base medium, serum, blood and endotoxin. The artificial test soil may optionally contain bilirubin and/or mucin or carbohydrate.

In a preferred embodiment, the artificial test soil comprises: base medium, up to 20% v/v serum; up to 10% v/v blood and up to 2,000,000 EU/ml endotoxin. If present, the bilirubin will be in the amount of about 1,000 nmoles/ml and the mucin or carbohydrate will be in the amount up to 10,000 µg/ml.

The base medium can be any medium that mimics physiological human fluids. A preferred base medium is RPMI. The serum can be derived from any serum source. A preferred serum is calf serum. The blood can be from any source and is preferably whole blood. A preferred blood is sterile sheep blood. The endotoxin can be derived from any source. A preferred endotoxin is derived from lipopolysaccharride (LPS), preferably purified LPS from a gram negative bacterium, and preferably from *Escherichia coli*. The ATS may optionally contain bilirubin, for example when preparing a soil that mimics the gastrointestinal site. When present, the bilirubin is preferably derived from oxgall bile such as bovine oxgall bile. The ATS may also optionally contain a carbohydrate source. When present, the carbohydrate is preferably derived from L-Glutamine, glucose or oxgall bile. The ATS may also contain a source of sodium which is added to the RPMI base to provide osmolarity that mimics physiological solutions. The sodium source may be derived from sodium chloride, sodium bicarbonate and/or sodium pyruvate.

The ATS formulations of the present invention are based on experimental data representing the "worst-case" soil levels from patient-used medical devices and therefore represents a standardized soil formulation that would be applicable to a wide range of medical device simulated-use testing.

In a particular embodiment, the present invention provides an artificial test soil that mimics the gastrointestinal site (referred to herein as ATS-GI) comprising:

RPMI 1640
LPS
Calf Serum
Bovine Oxgall
Sterile Sheep Blood
Sodium Bicarbonate
Sodium-Pyvuvate and
L-Glutamine.

In another embodiment, the present invention provides an artificial test soil that mimics soil related to the lung site (referred to herein as ATS-B) comprising:
RPMI 1640
LPS
Calf Serum
Sterile Sheep Blood
Sodium Bicarbonate
Sodium-Pyvuvate and
L-Glutamine.

The preparation of the ATS-GI formulation and the ATS-B formulation is detailed in Example 2. These ATS soils have reproducible formulations that provide a "worst-case" soil challenge as outlined by FDA recommendations for test soils. Example 3 and Table 5 summarize the composition of the ATS-GI and ATS-B formulations compared to Edinburgh soil, 10% serum, 100% blood test soil and worst-case values from patient-used samples. It is apparent from this data that ATS is the test soil that best mimics the levels of those physiological parameters measured compared to "worst-case" soil from a patient-used medical device. From the data on worst-case patient-used samples and patient-used cleaned flexible endoscope samples, it has been possible to determine the worst-case, average and benchmark for cleaning criteria as shown in Example 4.

The need for an appropriate soil challenge has been recognized by governing agencies such as the FDA, but an acceptable standardized test soil has not been achievable due to lack of data for patient-used worst-case soil determinations. Because the components used in making the ATS formulations are well defined; RPMI is tissue culture medium that is chemically defined, and the other components including serum, blood, oxgall bile and purified endotoxin are all commercially available, standardization of the ATS formulations is feasible. Each batch of a particular ATS formulation would be analyzed to ensure it was within 5% of the expected values as outlined in Example 2. Other ATS formulations may be prepared as needed within the ranges of the components outlined and/or other physiological parameters that might be measured from medical device samples after patient-use.

The inventor's experimental data from patient-used devices (Example 1) indicates that for flexible endoscopes the <10:1 ratio of protein to salt is actually more reflective of actual in-use conditions than what Jacob et al (1999) is recommending (100% fetal bovine serum). Furthermore, Jacob et al (1999) indicate that "The choice of an "appropriate" test soil is difficult to define". The present invention, ATS, uses experimentally derived data to meet this need. ATS is the first soil formulation that is based on experimental data from patient-used medical devices and reflects a soil formulation consistent with what these devices would be expected to harbor from actual clinical use.

2. Uses of the ATS

The ATS of the present invention can be used to evaluate the efficiency of a reprocessing method on a device, such as a medical device. Accordingly, the present invention provides a method of evaluating a reprocessing method on a device comprising:
(a) applying an artificial test soil (ATS) comprising base medium, serum, blood and endotoxin to the device;
(b) subjecting the device to the reprocessing method to be evaluated; and
(c) determining the presence or absence of at least one contaminant on the device.

The term "contaminant" means any material that should not be present if the reprocessing method worked efficiently. The presence of a contaminant indicates that the process is not efficient or the operator has not properly performed the process. Examples of contaminants that may be detected include blood or hemoglobin, protein, glucose, endotoxin, bilirubin, sodium and chloride ions and leukocyte esterase. Preferably, the presence of more than one contaminant is evaluated.

The phrase "reprocessing method" means any process that is purported to clean and/or disinfect/sterilize a device and includes: (a) cleaning the device to remove soil, and/or (b) disinfection/sterilization which kills microorganisms. The process can include apparatuses such as washers/disinfectors, sterilizers and/or compositions such as detergents, disinfectants and sterilants. A person skilled in the art would appreciate that reprocessing of previously used medical devices preferably includes cleaning of the device, which is most preferably followed by disinfection/sterilization.

In one embodiment, the ATS can be used to evaluate the efficiency of a reprocessing method on the killing of microorganism(s).n Accordingly, the present invention provides a method of determining whether a reprocessing method can kill a microorganism on a device comprising:
(a) inoculating an artificial test soil (ATS) with a microorganism wherein the ATS comprises base medium, serum, blood and endotoxin;
(b) applying the inoculated ATS to the device;
(c) subjecting the device to the reprocessing method to be evaluated; and
(d) determining the presence or absence of the microorganism on the device.

The presence of a microorganism indicates that the process is not efficient or the operator has not properly performed the method.

The above described methods have a variety of applications some of which are outlined below.

In one example, the ATS formulations of the invention can be used as standardized test soils by manufacturers when testing equipment such as cleaner/disinfectors and sterilizers, as well as for medical devices where reprocessing protocols need to be developed. Examples of medical devices include flexible endoscopes, narrow lumened accessory devices used in gastrointestinal or respiratory tract such as cannulatomes, balloon catheters or other accessory devices used for endoscopic procedures. In addition, the ATS formulations can be used by manufacturers needing to perform simulated-use evaluations for comparative testing of detergents, disinfectants or sterilants for medical device reprocessing.

For microbial killing-efficiency testing, the test microorganisms would be suspended in ATS to the desired concentration (most commonly $10^6$ viable organisms/device) and inoculated onto the medical device (or appropriate test carrier) for evaluation. The proposed applications would include; inoculation of the ATS (with or without microorganisms) onto a test medical device followed by up to 24 hours of drying to provide a "worst-case" challenge. Following the guidelines outlined in AAMI TIR#12 (1994), the ATS would act as the inorganic/organic challenge for this protocol. After air drying on the test carrier, the soil may also be fixed using 2.5% glutaraldehyde to provide a greater challenge for washing/detergent testing. This mimics what might occur in actual patient-use when devices are not adequately cleaned and are high-level disinfected using glutaraldehyde (2.0 to 2.5%) solutions. Furthermore, the ATS can be made up to contain up to 400 ppm hard water to meet FDA requirements for hard water testing. Because the composition of the soil is multi-facetted, it allows manufacturers to assess a wide variety of factors including; protein, hemoglobin (blood), bilirubin, carbohydrate, endotoxin, sodium and chloride ions. This allows manufacturers to assess relative efficacy of a reprocessing method on various soil components.

In another example, the ATS will also be used as a positive control in a test kit for cleaning validation that can be used in hospitals and other institutions to: 1) ensure adequacy of cleaning of medical devices as part of a quality assurance program, and 2) to ensure staff training competency. Accordingly, the present invention provides a cleaning validation test kit comprising the artificial test soil of the invention and an indicator to determine if the contamination has been adequately removed from the medical device. The indicator can be any indicator that can detect the presence of a contaminant. Preferably, more than one indicator is used, each one detecting the presence of a different contaminant. More preferably, a single indicator strip is used that detects the presence of more than one contaminant. Examples of the latter include a chemi-strip that can detect blood, protein and leukocyte esterase.

Using the test kit of the invention, samples are taken of the cleaned medical device, and tested using Chemi-strips for blood, glucose, protein and leukocyte esterase. The result from the cleaned device is compared to the positive control which consists of the ATS soil. Any medical device samples that flag any of the tests as positive should be recleaned before proceeding to the disinfection and/or sterilization step of device reprocessing. The clinical applicability of this test kit has been validated using in-use samples. The raw data from patient-used scopes pre and post cleaning that was used for this validation has been included in Example 5.

An advantage of the cleaning validation kit of the invention is that more than one parameter is evaluated, making it more sensitive than only testing for one soil parameter. In addition, the enzymatic detergents frequently used for reprocessing of medical devices will cause the leukocyte esterase and protein tests to flag as positive. Thus the kit can not only ensure that patient material has been adequately cleaned, it can also provide some assurance that rinsing has been adequate to remove any residual enzymatic detergent. Currently there are no test methods that allow such determinations to be made. The test kit of the invention provides a wider range of test parameters (blood, protein and leukocyte esterase) compared to the few published methods (Verjat et al 1999, Kruger 1997) that detect protein only. In addition the test kit can detect if there is residual enzymatic detergent (of formulations containing enzymes in concentrations adequate to trigger the protein and/or leukocyte esterase flags) remaining which is something other test kits cannot do. Furthermore, the benchmarks to validate the usefulness of the Chemistrip test method for protein and hemoglobin (Example 4) has been provided for the kit whereas similar validations are not provided for other published methods. An example of the test kit methodology is included in Example 6. The advantages of the ATS test soil and the test kit method are outlined below:

ATS:
1) ATS is reproducible and mimics "worst-case" soil levels expected from patient-use of medical devices.
2) ATS can be used for training of staff involved in medical device reprocessing and using ATS as the device soil reduces the risk of trainee exposure to infectious material during training.
3) ATS can be used for simulated-use testing with or without test organisms (ie same soil for cleaning validation testing and microbial load reduction testing).
4) Allows quantitative relative assessment of protein, blood, carbohydrate, bilirubin, sodium/chloride ions and endotoxin by standard chemistry assays.

Kit:
1) The test kit is rapid as the dip-strips require only 60 seconds for colour development. Therefore for in-use environments where time is critical it can realistically be performed by users.
2) The test evaluates the actual patient-used medical device for cleanliness in a non-destructive fashion (i.e., it is a DIRECT test NOT an indirect test of cleanliness of the medical device).
3) The achievable benchmarks have been validated by clinical in-use testing.
4) The kit measures four independent test parameters (blood, protein, glucose and leukocyte esterase) as such provides a more stringent assessment of cleaning compared to tests that evaluate only one parameter (eg protein only).
5) Device soiling with ATS combined with the kit testing of post-cleaning provides a very good tool for competency assessment of reprocessing staff.

In summary, Artificial Test Soil (ATS) is a composition that can be used for:
1) "simulated-use" testing of re-usable medical devices for manufacturer's developmental testing where the ATS represents a reasonable inorganic/organic challenge that mimics "worst-case" in-use soiling, and allows assessment of protein, blood (hemoglobin), carbohydrate, bilirubin (ATS-GI), sodium or chloride ions, and endotoxin.
2) positive control for a cleaning validation test kit to be used by hospital/health care users, to validate that the cleaned medical device is clean enough to proceed with disinfection/sterilization.
3) Inoculation soil for staff training where the ATS is used to soil the medical device, and in combination with the cleaning validation test kit is used to assess the trainee's ability to adequately reprocess the soiled device.

The following non-limiting examples are illustrative of the present invention:

EXAMPLES

Example 1

Worst-case Soiling Levels for Patient-Used Flexible Endoscopes Before and After Cleaning The soiling levels of patient-used narrow lumened flexible endoscopes, were assessed for bronchoscopes, duodenoscopes and colonoscopes. The effect of cleaning on the soil composition and concentration was evaluated.

Design

Suction channels from ten each of bronchoscopes, duodenoscopes used for endoscopic retrograde cholangiopancreatography (ERCP), and colonoscopes were assessed immediately after patient-use (PRE) for the levels of bilirubin, hemoglobin, protein, sodium ion, carbohydrate, endotoxin and viable bacteria. Another 10 suction channels of each type of endoscope were evaluated for the same components after routine cleaning but before processing by high-level disinfection or sterilization for subsequent clinical use (POST).

Materials and Methods

Endoscope Sampling

The types, dimensions, procedure performed, and procedure duration of the endoscope samples in this study are given in Table 1. All of the endoscopes were manufactured by Olympus Corp. (Lake Success, N.Y., USA). The models of colonoscopes included; EVIS-video CF-100L, and CF-20L (non-video), the side-viewing duodenoscope models used for endoscopic retrograde cholangio-pancreatography (ERCP) procedures included; JF-IT20, TJF-130 video, and JF-IT10 whereas the bronchoscope models included; BFP30D and BFJP20D. One set of endoscopes (called the PRE set) was sampled immediately after patient-use (no rinsing or cleaning), the second set of endoscopes was sampled after routine cleaning had been performed (called the POST set).

Endoscope Cleaning Procedures

The procedure for cleaning the POST colonoscopes and side-viewing ERCP duodenoscopes was; immediately after use, the suction channel of the patient-used endoscope was rinsed with approximately 10 mls of tap water, the endoscope was kept moist and transported within 20 minutes to the reprocessing area where is was cleaned by washing the outside with gauze dipped into enzymatic detergent prepared per the manufacture's instructions (Aseptizyme, Huntington Laboratories of Canada Ltd., Bramalea, ON), and suctioning approximately 10 mls of tap water through the suction channel, followed by 10 mls of enzymatic detergent. The suction channel was then brushed three times with an appropriate size endoscope brush (Endoscopy Support Services Inc. Brewster, N.Y.) dipped in enzymatic detergent and finally the endoscope suction channel was rinsed with approximately 25 mls of tap water. For side-viewing duodenoscopes, the elevator wire channel was rinsed with 5 mils of enzymatic detergent followed by 5 mls of tap water. The POST samples were taken at this point from the suction channel prior the endoscope being placed into an automated endoscope reprocessor.

Bronchoscopes were reprocessed in a different area of the hospital and the cleaning procedure used was slightly modified. The bronchoscope was flushed immediately after use with use-diluted Aseptizyme and a one-sided brush passed once through the suction channel. The endoscope was kept moist and transported to the reprocessing area within 20 minutes. The bronchoscope was then brushed with a single-ended brush that was dipped in Aseptizyme each time and pulled through the suction channel a total of 6 times. The POST samples were taken at this point from the suction channel prior the endoscope being placed into an automated endoscope reprocessor.

Sample Collection from Suction Channel of Flexible Endoscopes

For both PRE and POST sets, a sterile 2.7 mm channel cleaning brush (Endoscopy Support Services Corp., Brewster, N.Y.) appropriate for the types of flexible endoscopes studied was used for specimen collection. The brush was passed up and down the channel three times, then was aseptically cut off with sterile scissors and the brush portion collected into a sterile container. Ten mls of sterile distilled water was rinsed through the channel and collected in the same sterile tube with the brush.

Suction Channel Sample Processing

The sample from the suction channel (containing the brush) was mixed for 1 minute at room temperature using a vortex mixer. Viable counts were performed on this material immediately upon receipt. For other analytical tests, a portion of the sample was removed and sonicated in a Branson 1200 (Fisher Scientific, Ottawa, ON) ultrasonic water bath at room temperature for 5×1 minute exposures (Alfa et al., 1996) to insure solubilization of as much material as possible. A 2 ml aliquot was centrifuged at 600×g for 10 minutes at 4° C. to pellet any insoluble material. Removal of insoluble material was necessary prior to analyzing samples on the autoanalyzer to prevent "plugging" of the analyzer. The supernatant was removed to a separate sterile tube and used for analysis of protein, endotoxin, carbohydrate, hemoglobin, bilirubin, and sodium ion. Unused portions of the sample were stored at −70° C.

Bacterial Culture

Samples from patient-used flexible endoscopes were cultured by preparing serial 1:10 dilutions in tryptic soy broth (TSB) and then inoculating 100 $\mu$l of each dilution onto a chocolate agar (CHOC) plate. These inoculated CHOC plates were incubated at 35° C. in 5% $CO_2$ for 48 hours, then the detectable colonies were counted. The primary purpose of this was to determine the total viable bioburden (aerobes and facultative anaerobes), so no attempt was made to speciate the bacterial colonies detected.

Chemistry Analysis

The endoscope samples (after removal of insoluble particulate matter) were submitted to the Biochemistry Dept. at St. Boniface General Hospital, where they were processed using a Hitachi 717 autoanalyzer (Boehringer Mannheim, Laval, Quebec). The Hitachi-Plasma protocol was used for determination of hemoglobin (lower limit of reliable detection (LD; 10 $\mu$g/ml), and the Hitachi-Urine protocol was used for determination of; protein (LD; 10 $\mu$g/ml), bilirubin (LD; 0.5 nmole/ml), and sodium ion (LD; 10 $\mu$mole/ml). The protein determinations on samples with low levels of protein (<10 $\mu$g/ml) were re-tested using the Bio-Rad protein assay (LD; 0.5 $\mu$g/ml) to ensure reliability of protein determinations. Endotoxin determinations were performed by the Limulus amoebocyte lysate (LAL) pyrochrome chromogenic assay using the endpoint determination method by either North American Science Associates, Inc (NAMSA, Northwood Ohio) (all duodenoscope and colonoscope samples) or in the laboratory (all bronchoscope samples) using the LAL chromogenic assay according the manufacturer's directions (Associates of Cape Cod Inc., Falmouth, Mass.). The LAL assay kit contains negative and positive controls which were included in each assay, and the standard curve was prepared using the internal endotoxin reference standard provided. The standard curve ranged from a lower limit of 0.03 EU/ml up to 1 EU/ml upper limit of detection. Samples falling above the upper limit were diluted and retested to ensure the absorbance readings obtained fell within the linear portion of the standard curve. The carbohydrate assay was done according to the phenol-sulfuric acid method described by Liu et al (1994), using glucose for the standard curve. Carbohydrate was included in the soil analysis as it has been shown to indicate the presence of "bio-film" material.

Statistical Methods

Statistical analysis of data was performed using the GraphPad InStat software (GraphPad Software, San Diego, Calif.). The unpaired t test for continuous variables was used to compare the PRE and POST bacterial bioburden or soil loads in a given type of flexible endoscope. Linear regression was used to assess the correlation between procedure times and PRE bioburden loads.

Results

Recognizing that only soluble components could be quantified, the worst-case soil levels in the suction channels (the average surface area of these channels was 45.6 $cm^2$, 149.8 $cm^2$ and 192.0 $cm^2$ for bronchoscopes, duodenoscopes and colonoscopes, respectively) were; protein 115 $\mu$g/$cm^2$, sodium ion 7.4 $\mu$mole/$cm^2$, hemoglobin 85 $\mu$g/$cm^2$, bilirubin 299 nmoles/$cm^2$, carbohydrate 29.1 $\mu$g/$cm^2$, endotoxin 9852 EU/$cm^2$, and bacteria 7.1 ($Log_{10}$) cfu/$cm^2$.

Colonoscopes had 4–5 fold greater soiling on average compared to the other endoscope types. Routine cleaning reduced the levels of bilirubin to below the limits of detection for all endoscopes evaluated (limits of detection was <1 nmole/ml). After cleaning, residual hemoglobin was detectable in bronchoscopes only. After cleaning, the levels of protein, endotoxin, and sodium ion were all reduced by 5–10 fold for all types of endoscopes. Carbohydrate was reduced to less than the limit of detection for all endoscopes post cleaning, except the duodenoscopes. The average load of viable bacteria was reduced from 3–5 $Log_{10}$ cfu/$cm^2$ (this represents 5.9–9.5 $Log_{10}$ cfu/endoscope channel) after patient use to approximately 2 $Log_{10}$ cfu/$cm^2$ (this represents 3.2–5.3 $Log_{10}$ cfu/endoscope channel) after cleaning.

Sixty-one patient-used endoscopes were evaluated in this study consisting of; 10 Pre and 10 Post for each of the three types of flexible endoscopes evaluated (including bronchoscopes, side-viewing duodenoscopes, and colonoscopes (note; there were 11 PRE samples for the colonoscopes)). These samples were collected between August 1997 and February 1998. The endoscopy procedures, endoscope dimensions, and length of endoscopic procedures are given in Table 1. The average procedure time was 36 minutes, 32 minutes, 22 minutes for bronchoscopes, duodenoscopes and colonoscopes respectively. The bronchoscopies were almost always (90%) performed to obtain respiratory-secretions for microbiological culture, whereas the colonoscopies and duodenoscopies were usually performed to facilitate visualization or surgical procedures. All used endoscopes were processed in-house and transport time from the site of use to the reprocessing area was <20 minutes. There was no statistical correlation between the length of the procedure time and the PRE viable microbial load detected in any of the endoscope types (all linear regression correlation coefficients were <0.6).

The chemical analyses for the samples from patient used-endoscopes are given in Tables 2A, B and 3A, B. All assessments were determined based on the 10 mls sample volume (Tables 2A and 2B) and then converted to amount/$cm^2$ based on the inner suction lumen surface area for the specific type of endoscope from which the sample was obtained (Tables 3A and 3B). This was necessary to allow intra-endoscope comparisons, as the dimensions of bronchoscopes, duodenoscopes and colonoscopes are different (Table 1). All of the soil composition determinations likely represent underestimation of the soil on the actual lumen surface, as the sampling may not be 100% effective and the particulate matter had to be removed prior to chemical analysis. Although great effort was made to solubilize as much of the sample as possible by thorough mixing and sonication (details given in materials and methods section), the underestimation due to sample limitations must be recognized. Despite this caveat, it is apparent that there were high concentrations of most of the types of chemical components assayed in all PRE endoscope types (Table 2A, 3A). One component that was not present in high amounts in any of the endoscopes was hemoglobin. The hemoglobin level in blood from an average adult is approximately 122 mg/L (122,000 μg/ml) compared to the highest detected level in any PRE endoscope of 670 μg/ml. This suggests that despite the invasive nature of some of the procedures that the suction channel of such flexible endoscopes are unlikely to contain a large amount of residual blood immediately after the procedure. There were no gastro-intestinal (GI) bleeds that were assessed in the evaluation (Table 1) and although most flexible endoscopy procedures do not result in high blood concentrations in the suction channel, the endoscopies done on patients with GI bleeds might be expected to have more blood exposure. Bilirubin was only detected in duodenoscopes and colonoscopes and not bronchoscopes which is not surprising (Tables 2A, 3A) since bilirubin is found in the gastrointestinal tract but not the lungs.

The soil composition detected after cleaning of patient-used flexible endoscopes (POST samples) is given in Tables 2B and 3B. Despite reductions in most components measured, there were readily detectable levels of viable bacteria remaining. The duodenoscope samples were the only POST samples with detectable carbohydrate (Tables 2 and 3) which seems unusual. Although biofilm buildup might be one source of carbohydrate, it should also be noted that the Aseptizyme solution at working strength contained 562 ug/ml carbohydrate. From the data it was not possible to determine whether the POST levels of carbohydrate were actual biofilm or residual Aseptizyme. Neither of these sources of carbohydrate would be acceptable in a patient-ready reprocessed endoscope.

A summary of the chemical analysis for the average and worst-case (PRE) soil levels in patient-used endoscopes is given in Table 4.

Conclusions

These data demonstrated that cleaning effectively reduced or eliminated many components of soil but a substantial amount of viable bacteria and protein remained. Hemoglobin levels in PRE samples indicated that blood was not present in high concentrations in the suction channels of the majority of flexible endoscopes samples. Soil that mimics the "worst-case" composition from patient-used endoscopes would be ideal for simulated use studies for such medical devices.

The objective of experimental soil formulations for narrow lumened flexible endoscopes is to mimic "worst-case" soiling that might be present in a patient-used reprocessed flexible endoscope when it is subjected to high-level disinfection or sterilization. The use of such soil is to challenge the sterilization (or HLD) method to validate that it can provide adequate sterilization (or HLD) in the presence of some reasonable amount of organic matter. The problem is knowing what level of organic/$Na^+$ challenge is reasonable given that all medical devices MUST be cleaned prior to sterilization/disinfection. If a severe enough challenge is devised, no sterilizer may function adequately. The purpose of the soil challenge is NOT to cause sterilization failure, it is to provide some assurance that a "reasonable" soil challenge would not interfere with its ability to sterilize or disinfect viable microorganisms. If absolute cleaning of ALL parts of narrow lumened flexible endoscopes could be totally guaranteed for every patient-used flexible endoscope, then such simulated-use soil challenges for HLD and sterilization procedures would be unnecessary. At the present time given the design of the inner channels of long narrow-lumened flexible endoscopes and the lack of cleaning validation test methods, it is crucial that simulated-use testing include some reasonable soil challenge.

Since there is no published data on the types of soil levels (other than viable bacterial bioburden (Chan-Myers et al. 1997, Spach et al. 1993) that might be expected from patient-used flexible endoscopes, the aim of this study was to determine what type and amount of soil is found in the various types of flexible endoscopes after routine patient use both pre and post cleaning. This will form the basis for defining expected levels of soil pre and post cleaning, and will help establish cutoffs for "worst-case" soil challenges for sterilizer/HLD simulated-use studies and also better define expected cleaning efficacy benchmarks.

Discussion

The failure of sterilization and high-level disinfection procedures due to inadequate cleaning of flexible endoscopes has been well described (Bronowicki et al. 1997; Martin et al. 1994; Spach et al. 1993; Allen et al. 1987; Agerton et al. 1997; and Favero et al. 1996). Indeed recent surveys have indicated that cleaning is inadequately performed in 37/80 (46%) of hospitals (McCracken, 1995). Because reprocessed flexible endoscopes may have some soil within the lumens (especially if cleaning has not been scrupulous), testing bacterial killing efficacy of sterilizers and high-level disinfectant in the total absence of a soil challenge is not likely to be a true representation of actual reprocessing challenges when endoscopes are used in patient care. Despite the recognition that testing bacterial reduction of both high-level disinfectants and sterilants should include a relevant "soil" challenge (Martin et al. 1994; Pineau et al. 1997; AAMI, TIR #12; and Vesley et al. 1992), there is little experimental data on what the composition of an appropriate test soil for flexible endoscopes should be. The data presented here demonstrates that the suction channel from a patient-used flexible endoscope has a wide range of components present which include; hemoglobin, bilirubin (except bronchoscopes), protein, sodium ion, carbohydrate, endotoxin and viable organisms. The concentrations of soil components determined in this study may represent underestimations of the actual suction channel concentrations. Although brush/fluid sampling of the suction channel is a better sample method than flushing with fluid only (fluid samples have been shown to represent about 3% of channel bioburden (Hanson et al. 1990)), it still may only represent a fraction of the material within the suction channel. In addition, the test methods for chemistry analysis required that insoluble material be removed by centrifugation otherwise the autoanalyzer could be damaged. As such only solubilized material could be quantitated. Since visible inspection indicated that there was insoluble particulate matter particularly in the PRE colonoscope samples, the chemistry analysis may be underestimated. Despite these caveats, these data represent the best possible estimation of the soil burden in patient-used flexible endoscopes. Given that the data may represent an underestimation of the worst-case soil within the suction lumen, it seems reasonable to choose the "worst-case" soil level from the range of PRE samples of patient-used endoscopes to use as a "benchmark" for the "worst-case" test soil for flexible endoscopes for cleaning validation and sterilizer efficacy. Test soils with a blood or serum component have been recommended Jacobs et al. 1998), but it is apparent from the "worst-case" patient-used soil that the highest level of blood detected (as measured by hemoglobin) is substantially less (0.67 mg/ml) than would be present in a soil such as Edinburgh soil which is composed of 50% blood (Based on a hemoglobin concentration in human blood of 122 mg/ml, Edinburgh soil would be expected to have approximately 65 mg/ml hemoglobin). Indeed such high blood levels, as are found in Edinburgh soil, may be most appropriate for intravascular catheter testing or if one were trying to mimic an intestinal bleed. As indicated from Table 1 none of the 20 patients in the study that had colonoscopies had a GI bleed. The data indicates that a reasonable soil load for hemoglobin (blood) would be 86 ug/cm$^2$ (0.67 mg/ml). Likewise the soil formulations based only on serum (18,21) fail to incorporate the level of hemoglobin that is found in patient-used endoscopes.

Recently issues have been raised about the protein to sodium ion (Na$^+$) ratio of test soils Jacobs et al. 1998). Despite the lack of data from patient-used endoscopes, recommendations for use of protein/Na$^+$ ratios (>10:1) mimicking those found in serum have been recommended Jacobs et al. 1998). From the experimentally determined data it is apparent that an optimal ratio of protein/Na$^+$ that would mimic worst-case conditions for patient-used narrow lumened flexible endoscopes would be 115 $\mu$g protein/7.5 umole Na$^+$ per cm2, (2,200 $\mu$g protein/34 $\mu$mole Na$^+$ per ml). Comparison of the soil/cm$^2$ for different types of colonoscopes is the most appropriate approach, since the worst-case concentration from a bronchoscope compared to a duodenoscope will be different because the 10 ml sample came from a much smaller surface area when from a bronchoscope (660 mm×2.2 mm) compared to a duodenoscope (1490 mm×3.2 mm) or a colonoscope (1910 mm×3.2 mm). As reported by Jacobs et al (1998), serum contains 72,000 $\mu$g/ml protein and 3,000 $\mu$g/ml Na$^+$, which has a 24:1 ratio of protein/Na$^+$. The samples from the worst-case patient used endoscopes contained 2,200 $\mu$g/ml and 689 $\mu$g/ml Na$^+$ which has a 3.2:1 ratio of protein to Na$^+$. In contradiction to Jacobs et al's (1998) recommendation that test soils for flexible endoscopes should have a protein/Na$^+$ ratio of >10:1, it appears that actual worst-case soil samples from patient-used endoscopes have <10:1 protein/Na$^+$ ratio. As Jacobs et al's (1998) report points out at this type of protein/Na$^+$ ratio, crystal formation could be expected to occur. Therefore, in patient-used endoscopes the previously published problems encountered with crystal formation (Hanson et al. 1990; Abbott et al. 1956; and Royce et al. 1961) may be more of a problem than Jacobs et al (1998) have indicated. As pointed out by Jacobs et al (21), ALL flexible endoscopes should be cleaned prior to attempts at HLD or sterilization. As shown by the patient-used endoscopes described herein, even after cleaning, the protein/Na$^+$ ratio is NOT>10:1. As pointed out by Jacobs et al (1998) and many others (Rutala et al. 1998; Chan-Myers et al. 1997; DesCoutaux et al. 1995; Alfa et al. 1997; Alfa et al. 1998; McCracken 1995; Agerton et al. 1997; Alfa et al. 1996; Favero et al. 1996; and Vesley et al. 1992), scrupulous attention to cleaning of flexible endoscopes cannot be overemphasized. Because of the detrimental effect of Na$^+$ on gas sterilization (Alfa et al. 1997; Alfa et al. 1998; Alfa et al. 1996; Jacobs et al. 1998; Hanson et al. 1990; Abbott et al. 1956; and Royce 1961) the presence and/or buildup of Na$^+$ within patient-used flexible endoscopes warrants further study.

Although bilirubin was not detected in bronchoscopes, it was detectable in both colonoscopes and duodenoscopes, and an appropriate level for test soil would be 16 nmoles/cm$^2$. The data indicate that a protein level of approximately 115 $\mu$g/cm$^2$ is a reasonable estimate of the worst-case soil expected from patient-used flexible endoscopes.

Although both PRE and POST samples from the patient-used flexible endoscopes had some surprisingly high endotoxin levels, from a reprocessing perspective, the data indicate that this is a useful component for ATS as it appears to remain despite reprocessing of the patient-used devices.

Although normal cleaning decreased both hemoglobin and bilirubin to below the limit of detection in duodenoscopes and colonoscopes, there were still detectable levels of protein, endotoxin, and viable bacteria in all endoscopes tested. For all endoscope types, cleaning caused a significant reduction in the viable bioburden. Using an unpaired t test, the mean difference in Log$_{10}$ cfu for PRE and POST viable counts was 2.9 with a 95% Confidence Interval (CI$_{95\%}$) of 2.3 to 3.5 and p<0.0001 for colonoscopes, a mean difference of 1.2 with CI$_{95\%}$ of 0.03 to 2.4 and p=0.0451 for duodenoscopes, a mean difference of 1.3 with $CI_{95\%}$ of 0.4 to 2.2 and p=0.0068 for bronchoscopes. Despite cleaning there was significantly higher concentrations of residual hemoglobin, sodium ion, protein, endotoxin and viable bacteria within the bronchoscope channels compared to duodenoscopes or colonoscopes (Table 3). These data suggest that there may be material within the bronchoscope channels that is more difficult to remove compared to the other two types of flexible endoscopes. The bronchoscopes in our center are processed differently from the duodenoscopes and colonoscopes in that the former were submitted for ethylene oxide sterilization after high-level disinfection with 2% glutaraldehyde. The colonoscopes and ERCP duodenoscopes received peracetic acid treatment using the STERIS SYSTEM 1 processor most of the time with only occasional glutaraldehyde high-level disinfection in automated endoscope reprocessors, and they were not ETO sterilized. Although high levels of carbohydrate were not detected in bronchoscopes before or after cleaning, there may still be a buildup of residual soil within these endoscopes similar to that described by Tucker et al (1996) as a result of the cross-linking of proteins due to glutaraldehyde. The residual viable bioburden after cleaning was significantly higher (using the Tukey-Kramer multiple comparisons test) in bronchoscopes compared to duodenoscopes (p<0.05) and colonoscopes (p<0.001). All these factors indicate that the bronchoscopes have the greatest amount of residual material post cleaning. Since the bronchoscope suction channel is shorter than that of a colonoscope, and shorter as well as less complex than that of a duodenoscope (Table 1), the difference in the POST samples may represent buildup of soil in bronchoscopes that is more difficult to remove. This finding should not be generalized as it may be unique to our institution due to different bronchoscope reprocessing procedures compared to other flexible endoscopes.

Cleaning validation for reprocessed flexible endoscopes would be ideal to ensure that adequate cleaning has been performed. Recently there have been attempts to develop test methods that would provide a means of testing cleaning efficacy based on a color change test for protein (Kruger, 1997) or using microscopic examination (DesCoutaux et al. 1995). The protein based test attempted to establish "unacceptable cutoffs" and reported that >200 $\mu g/10$ $cm^2$ was an unacceptable protein load (Kruger, 1997). This translates to a cutoff of >20 $\mu g/cm^2$ for protein. Compared to the data from patient-used endoscopes, this cutoff appears insensitive, because post-cleaning, none of the flexible endoscopes had residual protein that was this high. For duodenoscopes and colonoscopes that had been cleaned, the data indicates that the worst-case protein concentration was 2.3 $\mu g/cm^2$, therefore, it seems that a better cutoff for unacceptable protein would be >5 ug/$cm^2$. If the cutoff were 5 ug/$cm^2$ it is apparent that some of the bronchoscopes would fail this cut-off criteria post-cleaning (Table 3) Although residual organisms and protein are primary concerns in cleaned medical instruments, the data here indicates that hemoglobin (or blood), and endotoxin can also remain after cleaning (Tables 2,3). Cleaning validation studies should attempt to assess a number of soil parameters and not focus on protein only.

The viable bioburden levels detected in this analysis are similar to those previously reported from patient-used flexible endoscopes (Alfa et al. 1994; Jacobs et al. 1998). Unlike readily cleaned rigid medical devices (both lumened and non-lumened), the levels of bioburden in flexible patient-used endoscopes reach high levels (up to $10^9$ cfu/device for PRE colonoscopes). Even after routine cleaning, the residual levels of bioburden remaining in the channel of flexible endoscopes are substantially higher (Table 3) than those found either on or within the lumens of rigid, easily cleaned devices (Chan-Myers et al. 1997; Pflug et al. 1991). Although Chan-Myers et al (1997) have suggested that a lower challenge with little organic/inorganic soil might better mimic routine in-use conditions for rigid easily cleaned devices, this would be inappropriate for narrow lumened flexible endoscopes. The basic concept promoted by the present invention—which is not to use test soils that go far beyond the level of what would be expected in actual use—is valid. Indeed, the experimental data indicates that if trying to simulate "worst-case" clinical-use soiling levels, then full-strength Edinburgh soil or Hucker's soil are inappropriately severe challenges for narrow lumened flexible endoscopes.

In summary, the above experimental data demonstrates the average and worst-case concentrations/$cm^2$ for soil that would be expected from patient used endoscopes. Based on this bench-mark data, it is possible to design studies that better mimic "worst-case" challenges for simulated-use testing. Furthermore, benchmarks for soil levels that are achievable using routine cleaning methods have been established.

Example 2

This example describes specific artificial test soil formulations.
1. Soil-Gastrointestinal Formula The artificial test soil-gastrointestinal formula (ATS-GI) is useful for tests related to GI soiling.
Material Required
Equipment
    1.0 Liter sterile glass bottle
    1.0 Liter graduated cylinder
    Sterile 2 mL, 5 mL, 10 mL pipettes
    Weigh boats
    Balance
    1.5 mL eppendorf tubes
    0.22 $\mu m$ PES filter unit
Media
    LPS Powder
    Calf Serum
    Bovine Oxgall Powder
    RPMI 1640 Powder
    Sodium Bicarbonate Powder
    100 mM Na-Pyvuvate
    200 mM L-Glutamine
    Sterile Sheep Blood
    Sterile Distilled Water (~1 L)
Procedure
To prepare 1.0 Liter ATS-GI1
Prepare in Advance
1. Rehydrate 25 mg of LPS powder in 5 mL of sd $H_2O$. Aliquot into exactly 1000 $\mu L$ aliquots in 1.5 mL eppendorf tubes. Label with Lot # and date. Store at −20° C. or −70° C. until needed.
2. Heat inactivate the Calf serum by heating at 56° C. for 30 minutes.
ATS-GI1 Method
1. Into a 2.0 Liter glass beaker, add 20.0 g of Bovine Oxgall bile powder
2. Add 10.4 g of RPMI 1640 modified powder (with L-glutamine/without sodium bicarbonate).

3. Add 2.0 g of sodium bicarbonate powder.
4. Add 700 mL of distilled $H_2O$.
5. Mix well and add 10.0 mL of 100 mM sodium pyruvate (Na-pyruvate).
6. Add 10.0 mL of 200 mM L-glutamine.
7. Mix contents of beaker well. Pour into a graduated cylinder and QS to 894 mL with distilled water. Filter entire volume through a 0.22 µm membrane filter unit (Nalgene—Cat. # 167-0020) into a 2.0 L sterile bottle.
8. Using sterile technique, add 5.0 mL of sterile sheep blood.
9. Thaw 1–1.0 mL aliquot of 5 mg/mL *E. coli* LPS and using sterile technique add entire contents to the mixture.
10. Using sterile technique, add 100 mL of Heat Inactivated Calf serum. This procedure provides 1.0 Liter of sterile ATS-GI 1.

Perform sterility testing by incubating a 10.0 mL aliquot at 35° C. for 48 hours and then test for bacterial growth by sub-culturing onto a chocolate agar plate incubate at 35° C. in 5% $CO_2$ for 48 hours.

Applications
Cleaning Validation
  Apply to medical device or test carrier. Allow to dry at room temperature for 30 minutes–24 hours.
  Perform cleaning protocol.
  Assess residual soil parameters (e.g. Protein, hemoglobin, LPS, carbohydrates)
Disinfectant/Sterilant Efficacy
  Resuspend test organism in ATS-GI 1
  Apply to medical device or test carrier. Allow to dry at room temperature for 30 minutes–24 hours.
  Perform cleaning and/or disinfection/sterilization. (suitable time exposure)
  Rinse ×1 with PBS gently.
  Resuspend in sterile distilled water by mixing/sonicating.
  Quantitatively determine residual viable count. Assess residual parameters.

2. Bronchoscopy Formula

The artificial test soil bronchoscopy formula (ATS-B) is useful for tests related to bronchoscopy soiling.

Material Required
Equipment
  1.0 Liter sterile glass bottle
  1.0 Liter graduated cylinder
  Sterile 2 mL, 5 mL, 10 mL pipettes
  Weigh boats
  Balance
  1.5 mL eppendorf tubes
  0.22 µm PES filter unit
Media
  LPS Powder
  Calf Serum
  RPMI 1640 Powder
  Sodium Bicarbonate Powder
  100 mM Na-Pyvuvate
  200 mM L-Glutamine
  Sterile Sheep Blood
  Sterile Distilled Water (~1 L)
Procedure
To prepare 1.0 Liter ATS-B1
Prepare in Advance
1. Rehydrate 25 mg of LPS powder in 5 mL of sd $H_2O$. Aliquot into exactly 1000 µL aliquots in 1.5 mL eppendorf tubes. Label with Lot # and date. Store at −20° C. or −70° C. until needed.
2. Heat inactivate the Calf serum by heating at 56° C. for 30 minutes.

ATS-B1 Method
1. Into a 2.0 Liter glass beaker, add 10.4 g of RPMI 1640 modified powder (with L-glutamine/without sodium bicarbonate)
2. Add 2.0 g of sodium bicarbonate powder.
3. Add 700 mL of distilled $H_2O$.
4. Mix well and add 10.0 mL of 100 mM sodium pyruvate (Na-pyruvate).
5. Add 10.0 mL of 200 mM L-glutamine.
6. Mix contents of beaker well. Pour into a graduated cylinder and QS to 889 mL with distilled water. Filter entire volume through a 0.22 µm membrane filter unit (Nalgene—Cat. # 167-0020) into a 2.0 L sterile bottle.
7. Using sterile technique, add 10.0 mL of sterile sheep blood.
8. Thaw 1–1.0 mL aliquot of 5.0 mg/mL *E. coli* LPS and using sterile technique add entire contents to the mixture.
9. Using sterile technique, add 100 mL of Heat Inactivated Calf serum. This procedure provides 1.0 Liter of sterile ATS-B1.

Perform sterility testing by incubating a 10.0 mL aliquot at 35° C. for 48 hours and then test for bacterial growth by sub-culturing onto a chocolate agar plate incubate at 35° C. in 5% $CO_2$ for 48 hours.

Applications
Cleaning Validation
  Apply to medical device or test carrier. Allow to dry at room temperature for 30 minutes–24 hours.
  Perform cleaning protocol.
  Assess residual soil parameters (e.g. Protein, hemoglobin, LPS, carbohydrates)
Disinfectant/Sterilant
  Resuspend test organism in ATSB1
  Apply to medical device or test carrier. Allow to dry at room temperature for 30 minutes–24 hours.
  Perform cleaning and/or disinfection/sterilization. (suitable time exposure)
  Rinse ×1 with PBS gently.
  Resuspend in sterile distilled water by mixing/sonicating.
  Quantitatively determine residual viable count. Assess residual parameters.

Example 3
Comparison of ATS with Other Test Soils

The ATS-GI and ATSB formulations were compared with Edinburgh soil, 10% serum and 100% blood test soil.

Concerns about the impact of residual soil on sterilization have stimulated the development of a wide range of "soils" for simulated-use testing. These soil formulations range from challenges consisting of 10% serum (AAMI TIR # 12, 1994) to soils that mimic tissue culture conditions (Alfa et al 1996) to more exotic combinations such as Edinburgh soil (hog mucin, blood, egg) and Hucker's soil (peanut butter, evaporated milk, butter, flour, lard, dehydrated egg yolk, printers ink, saline and blood,) (AAMI TIR # 12, 1994, Jacobs et al 1998). Many of these soil formulations were developed to assess cleaning efficacy but are not necessarily the most appropriate for "simulated-use testing".

Design

To determine how well these soil formulations compared to either "worst-case" or "average" levels of soil from patient-used devices, the formulations were assessed for levels of bilirubin, hemoglobin, protein, sodium ion, carbohydrate, and endotoxin. These were compared to the levels of the same soil components found in samples from patient-used flexible endoscopes (as described in Example 1), to determine which test soil formulation would best mimic in-use organic/inorganic levels.

Materials and Methods

Test Soil Formulations

Edinburg soil was prepared by aseptically mixing equal volumes of a whole egg and whole sheep blood. The 100% blood test soil consisted of sterile Sheep blood. The 10% FBS test soil consisted of 10% (v/v) sterile bovine serum prepared by adding 10 mls sterile bovine serum to 90 mls sterile distilled water. The Normal saline consisted of phosphate buffered saline at pH 7.0.

Chemistry Analysis

The test soil samples were submitted to the Biochemistry Dept. at St. Boniface General Hospital, where they were processed using a Hitachi 717 autoanalyzer (Boehringer Mannheim, Laval, Quebec). The Hitachi-Plasma protocol was used for determination of hemoglobin (lower limit of reliable detection (LD; 10 g/ml), and the Hitachi-Urine protocol was used for determination of; protein (LD; 10 g/ml), bilirubin (LD; 0.5 nmole/ml), and sodium ion (LD; 10 mole/ml). The protein determinations on samples with low levels of protein (<10 g/ml) were re-tested using the Bio-Rad protein assay (LD; 0.5 g/ml) to ensure reliability of protein determinations. Endotoxin determinations were performed by the Limulus amoebocyte lysate (LAL) pyrochrome chromogenic assay using the endpoint determination method by either North American Science Associates, Inc (NAMSA, Northwood Ohio) (all duodenoscope and colonoscope samples) or in our laboratory (all bronchoscope samples) using the LAL chromogenic assay according the manufacturer's directions (Associates of Cape Cod Inc., Falmouth, Mass.). The LAL assay kit contains negative and positive controls which were included in each assay, and the standard curve was prepared using the internal endotoxin reference standard provided. The standard curve ranged from a lower limit of 0.03 EU/ml up to 1 EU/ml upper limit of detection. Samples falling above the upper limit were diluted and retested to ensure the absorbance readings obtained fell within the linear portion of the standard curve. The carbohydrate assay was done according to the phenol-sulfuric acid method described by Liu et al (1994), using glucose for the standard curve.

Results

The results are presented in Table 5 and are reported as amount per $cm^2$ as well as amount/ml. The amount/$cm^2$ are included as these would be reflective of ATS dried onto a device surface as part of the inoculation process when testing reprocessing methods.

Edinburgh soil contains 38 fold more hemoglobin/$cm^2$ than the worst-case soil levels detected in patient used endoscopes. In addition Edinburgh soil contains 19 fold more protein/$cm^2$ than the worst-case soil levels detected in patient-used endoscopes. While Edinburgh soil over represents hemoglobin and protein, it under represents bilirubin and endotoxin, as neither of these are present in Edinburgh soil, yet there are significant levels of both detected in patient-used medical devices (Table 5). The 100% blood test soil is similar to Edinburgh soil in that hemoglobin and protein are both over represented, whereas bilirubin and endotoxin are not present. The 10% FBS test soil does not contain bilirubin or endotoxin, nor does it contain hemoglobin. The Normal saline test soil only mimics sodium and chloride ion levels and does not adequately represent any of the other soil parameters including hemoglobin, bilirubin, protein, carbohydrate or endotoxin.

Conclusions

The results, shown in Table 5, indicate that the ATS best mimics the physiological parameters that simulate the "worst-case" soil from a patient used medical device. Edinburgh soil and 100% blood test soils over-represent some components while 10% FBS and Normal saline under-represent some components found in samples from patient-used devices. Of the six test soils evaluated, ATS-GI and ATS-B most closely simulate the levels of hemoglobin, bilirubin, protein, carbohydrate and endotoxin found in worst-case samples from patient-used devices.

Example 4

Benchmark Data for Flexible Endoscopes

FIGS. 1 to 6 summarize the benchmarks determined for "worst-case" soil and for post-cleaning levels achievable.

Reprocessing of medical devices preferably includes cleaning of the device, which is most preferably followed by disinfection/sterilization. Often problems in reprocessing that have led to transmission of infection from one patient to another are related to breaks in the cleaning procedure To provide a reliable approach to cleaning validation, it is necessary to first provide benchmark data. To reliably determine if endoscopes have been adequately cleaned, it is necessary to first establish what the achievable benchmarks are for a representative currently accepted routine cleaning method. The benchmark is defined as the average of the detectable levels of the soil component POST cleaning.

Design

The aim was to identify the highest possible concentration of a particular soil pre-cleaning, the average concentration expected, and the benchmark level of soil expected after routine cleaning. The highest level of soil pre-cleaning represents the "worst-case" level that a medical device would be exposed to from patient-use. Because the colonoscopes had the greatest soil level pre-cleaning, the data from this type of endoscope has been evaluated for "worst-case" and average determinations for hemoglobin, protein, bilirubin, carbohydrate, endotoxin, and viable bacteria. Since the sodium ion levels were highest for bronchoscopes, the worst-case, average and benchmark data for sodium ion were only presented for bronchoscope samples.

Materials and Methods

The sample collection and chemistry analysis of the samples has been described in Example 1. The data have all been presented as amount/$cm^2$ to represent the soil levels on the surface of the medical device being tested. The Worst-case and Average soil levels were determined for samples collected from patient-used colonoscopes prior to any cleaning. The benchmark levels were determined for samples collected from patient-used colonoscopes AFTER the standard cleaning protocol.

Standard Cleaning Protocol

The procedure for cleaning the POST colonoscopes was; immediately after use, the suction channel of the patient-used endoscope was rinsed with approximately 10 mls of tap water, the endoscope was kept moist and transported within 20 minutes to the reprocessing area where it was cleaned by washing the outside with gauze dipped into enzymatic detergent prepared per the manufacture's instructions (Aseptizyme, Huntington Laboratories of Canada Ltd., Bramalea, ON), and suctioning approximately 10 mls of tap water through the suction channel, followed by 10 mls of enzymatic detergent. The suction channel was then brushed three times with an appropriate size endoscope brush (Endoscopy Support Services Inc. Brewster, N.Y.) dipped in enzymatic detergent and finally the endoscope suction channel was rinsed with approximately 25 mls of tap water. For side-viewing duodenoscopes, the elevator wire channel was rinsed with 5 mls of enzymatic detergent followed by 5 mls of tap water. The POST samples were taken at this point from the suction channel prior the endoscope being placed into an automated endoscope reprocessor.

Results

Figure 2:
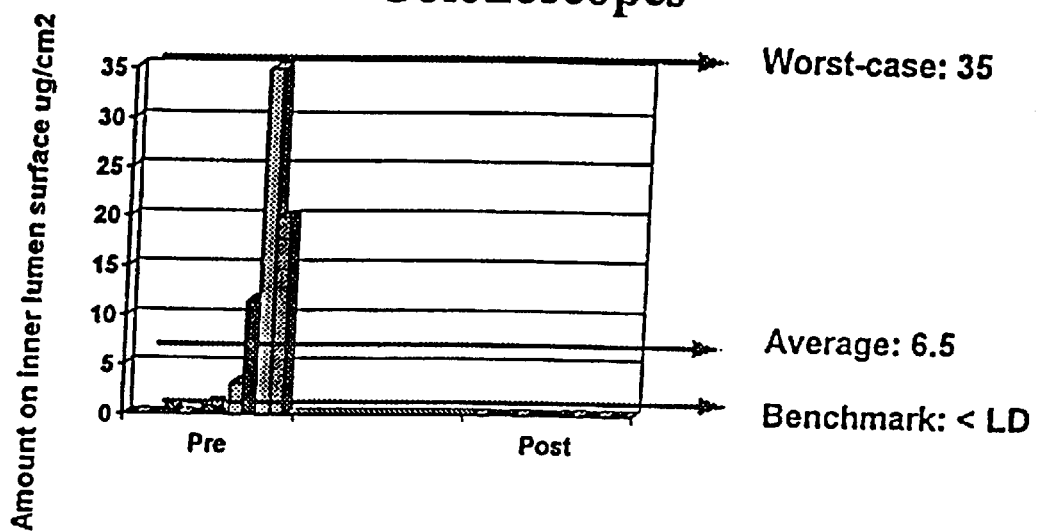
FIG. 2 is a bar graph showing the amount of hemoglobin present on colonoscopes.
Figure 3:
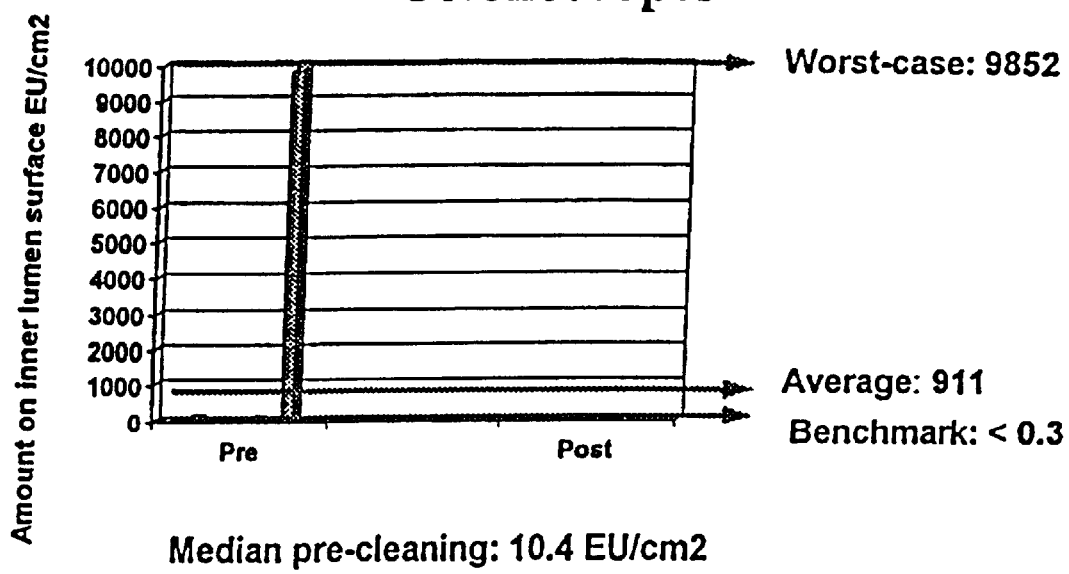
FIG. 3 is a bar graph showing the amount of endotoxin present on colonoscopes.
Figure 4:
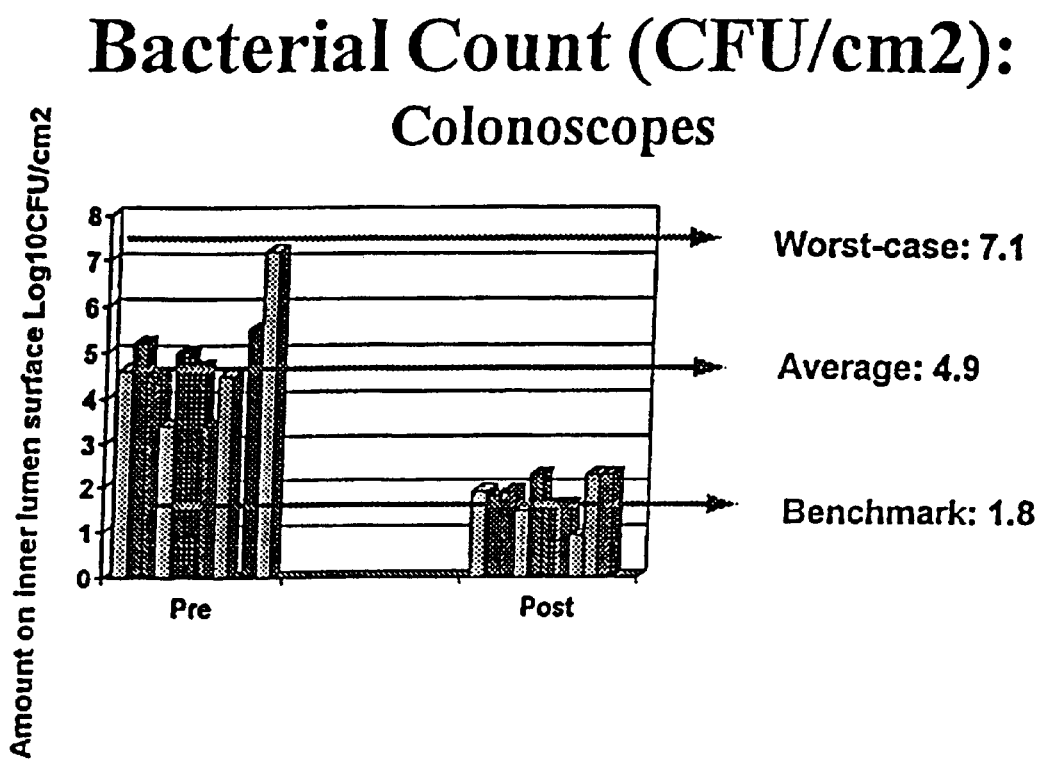
FIG. 4 is a bar graph showing the bacterial count on colonoscopes.
Figure 5:
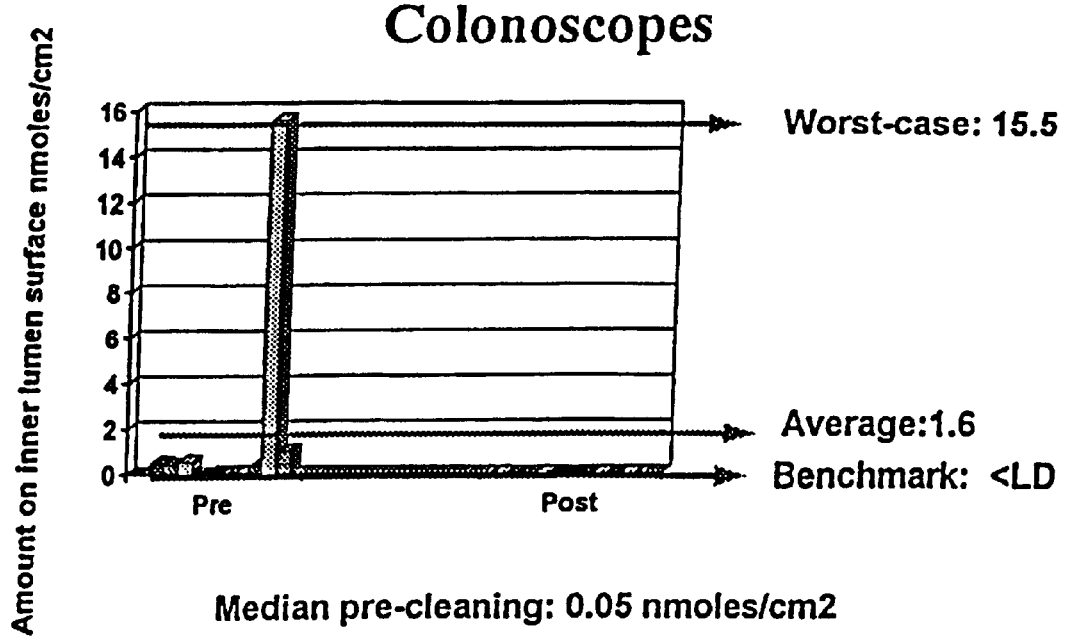
FIG. 5 is a bar graph showing the amount of bilirubin present on colonoscopes.
Figure 6:
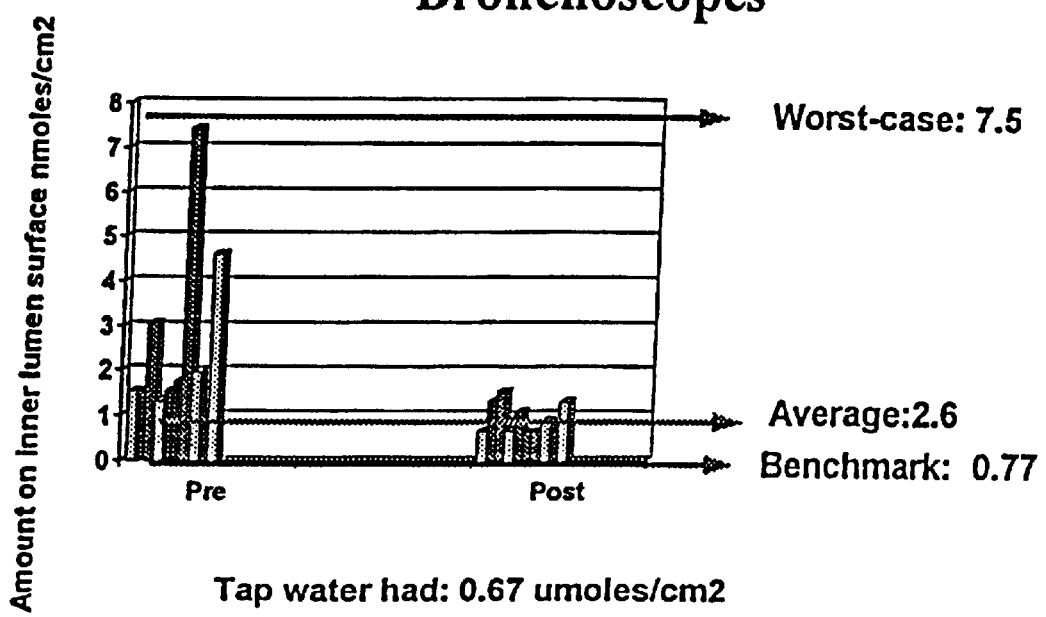
FIG. 6 is a bar graph showing the amount of sodium ions present on colonoscopes.

The worst-case, average and Benchmark data is presented for Protein in FIG. 1, Hemoglobin in FIG. 2, Endotoxin in FIG. 3, Viable bacteria in FIG. 4, Bilirubin in FIG. 5, and Sodium ion in FIG. 6. There was detectable protein in all 10 colonoscopes sampled PRE cleaning and in addition, all 10 had detectable protein POST cleaning. Although there was residual protein POST cleaning, the benchmark data indicate that by using a routine cleaning protocol <5 ug/cm$^2$ of protein should remain in even the colonoscopes which were the endoscopes showing the highest level of soiling PRE cleaning. The achievable benchmarks for hemoglobin, endotoxin and bilirubin should be less than the limit of detection for the assay methods used (FIGS. 2, 3 and 5). For sodium ions, the benchmark achievable is 0.77 umoles/cm$^2$ which is expected as it is similar to tap water levels. Since tap water was used for the final rinse of these devices, this is expected.

Discussion

The "worst-case" soil values were utilized in determining the concentrations of the various soil parameters for the ATS formulations. This approach addresses the FDA recommendation to do testing using "worst-case" situations, as the ATS formulations represent the "worst-case" soil that medical devices would be exposed to during actual clinical use. In addition, the Figures indicate the achievable soil parameters that can be achieved using routine cleaning practices. These post-cleaning levels become the benchmarks needed for the validation kit of the invention.

In all cases (except for sodium ion content) the colonoscopes had the highest "worst-case" amounts/cm$^2$ for protein, hemoglobin, endotoxin, bacterial counts and bilirubin as well as the highest amounts/cm$^2$ for achievable benchmarks post-cleaning. As such the data for colonoscopes only are presented. For sodium ion amounts/cm$^2$, the bronchoscopes presented the "worst-case" pre-cleaning and post-cleaning, therefore, the figure for sodium ion is derived from the bronchoscope data. These data demonstrate the clinically relevant benchmarks that are achievable for soil removal using a routine in-house cleaning protocol. These data are derived from 10 random replicates and as such should be representative of both "worst-case" soil levels and reasonable post-cleaning benchmarks.

Conclusions

Routine cleaning should provide an endoscope that has no detectable hemoglobin (or blood), bilirubin, or endotoxin. Although protein may remain POST cleaning, the level should be <5 ug/cm$^2$. Rapid cleaning validation tests should be able to reliably flag as negative when these benchmark levels are achieved.

Example 5

Chemistrip Raw Data from Patient-Used Endoscope Samples

This example examines the level of contamination on endoscopes pre and post cleaning. The samples were tested by sophisticated chemistry analysis tests to assess quantitatively the levels of protein, hemoglobin (blood), sodium ion, chloride ion and bilirubin. In addition each sample was tested by chemistrip "dip-strip" to determine which samples would cause the rapid test strips to flag as positive. From this data it is apparent that the leukocyte esterase, protein and blood test pads were most useful for flagging soil in the pre-cleaned samples (Tables 6, 7, and 8). The leukocyte esterase test pad detected 10/10 colonoscope samples, 5/10 duodenoscopes and 4/10 bronchoscope samples. The protein test pad detected 9/10, 5/10, and 6/10 of the colonoscope, duodenoscope and bronchoscope samples respectively. The blood test pad detected 10/10, 9/10 and 8/10 of the colonoscope, duodensocope and bronchoscope samples respectively. Of the 30 pre-cleaning samples tested (10 each of; colonoscopes, duodenoscopes and bronchoscopes), there were only two flexible endoscope pre-clean samples that did not flag any of the test pads on the Dip-strip. This correlates with the quantitative chemistry analysis of these two samples, as there was either no or very little protein, blood, bilirubin, carbohydrate or endotoxin in these samples indicating that they were relatively unsoiled compared to the other scope samples. Post-cleaning there were some patient-used scope samples that were flagged positive by at least one of the Dip-strip tests. This was most commonly observed for bronchoscope samples and may represent residual detergent as there were more positive leukocyte esterase positive tests post-cleaning (7/10) compared to pre-cleaning (4/10). When tested against several different types of enzymatic detergents (at the manufacturers recommended concentration for flexible endoscope reprocessing), leukocyte esterase flagged positive for Asceptizyme (Huntington Laboratories Canada, Bramalea, Ont.), Enzycare2 (STERIS Corp. Mentor, Ohio), and Klenzyme (STERIS Corp. Mentor, Ohio). Based on the average and ranges of patient-used soil levels for protein (Table 9) and hemoglobin (Table 10), the Chemistrip should give a positive reaction for both protein and blood for pre-cleaning samples for colonoscopes, duodenoscopes and bronchoscopes. Furthermore, it should be possible to achieve negative tests on the protein, and blood, for post-cleaning endoscope samples tested by the Chemistrip "Dip-strips". It should be noted that the glucose test pad has only been included because the currently manufactured Chemistrips have a four pad test strip that included the three main test pads the data indicated were important (leukocyte esterase, protein and blood). Because these Dip-strips are already commercially available the inventor has opted for using them rather than having special strips manufactured for the cleaning validation kit. Although ATS will cause the glucose test strip to flag positive, the pre and post sample analysis indicates that glucose pads are not as sensitive compared to the other 3 test pads as indicators of soil on patient-used endoscopes.

Example 6

Cleaning Validation Test Kit

Figure 7:
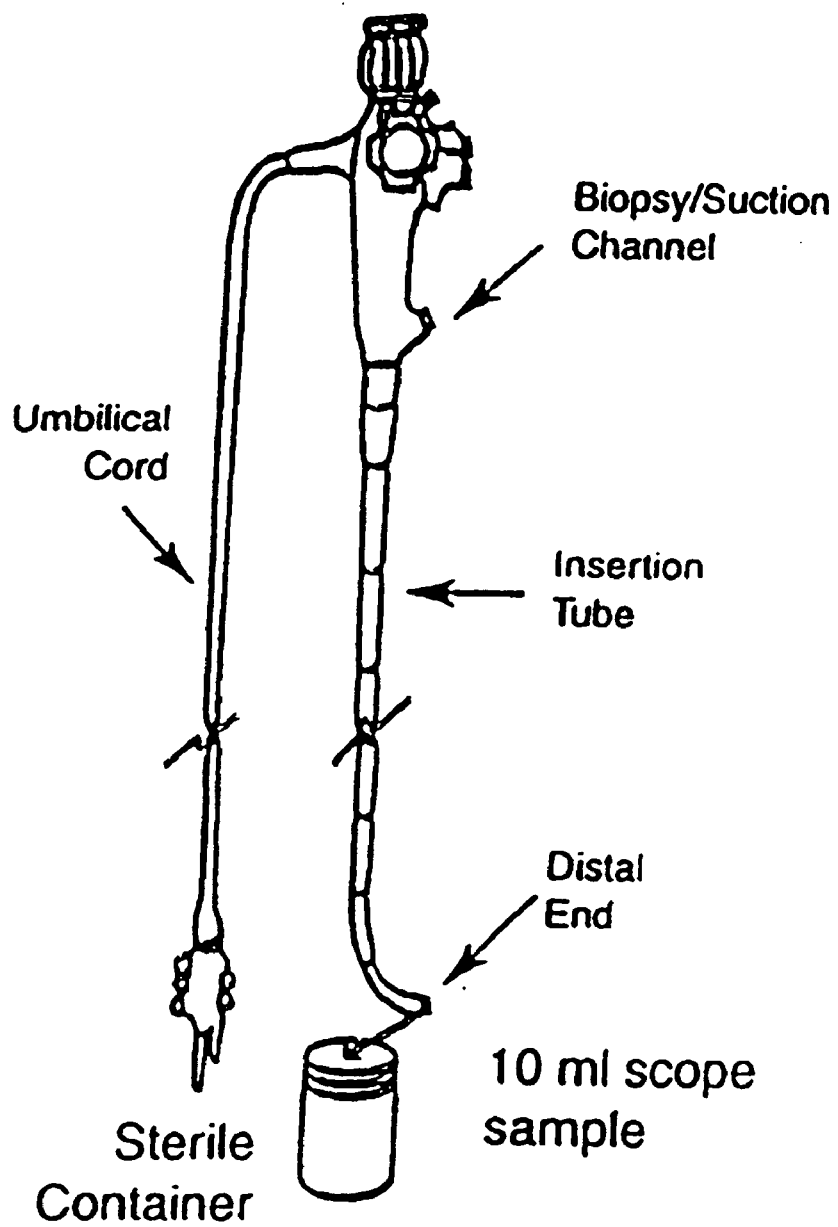
FIG. 7 is a schematic drawing showing the cleaning of a flexible endoscope.

This example illustrates how the test kit of the invention can be used to validate the cleaning of a flexible endoscope. As an example, the test kit can contain:

20 vials of ATS (positive control)
20 disposable channel brushes
25 test dip-strips
25 sample collection tubes
25 tubes of sterile water
25 disposable 5 ml plastic syringes
one test-strip colour indicator chart Test Method 1. Clean flexible endoscope using a routine cleaning process.
2. Open a tube of sterile water.
3. Draw up 5 mls of sterile water into one of the sterile 5 ml syringes provided.
4. Place the end of the flexible endoscope in one of the sterile sample collection tubes provided.
5. Inject the 5 mls of sterile water into the biopsy/suction channel port and collect the fluid as it exists the distal end into the sample collection tube (FIG. 7) (Keep this syringe, you need it later in step 8).
6. Dip one end of a disposable channel brush into the open container of sterile water to wet it.
7. Pass the wetted brush up and down the channel a total of 4 time (down-up, down-up), then discard the brush following your centre's guidelines for cleaning brush disposal.
8. Draw up another 5 ml aliquot of the sterile water into the syringe and inject it into the biopsy/suction port.
9. Collect this second 5 ml sample into the same container as the first 5 ml sample.

This 10 ml sample is your scope sample that will be tested.

10. Mix the scope sample.
11. Remove a test dip-strip from the kit and place it into the scope sample to completely wet the end that has 4 test "pads" on it.
12. Remove the test dip-strip and after 60 seconds compare it to the indicator chart to determine if there are any positive reactions.
13. Each day testing of scope samples is performed at least one positive control must be tested using the dip-strip to confirm that the strips are giving an appropriate colour reaction.

Interpretation

ANY colour change on ANY of the four pads of the test dip strip indicates that there is residual protein, blood, glucose or enzymatic detergent. The flexible endoscope should be RECLEANED before proceeding to the high-level disinfection or sterilization process routinely used in your centre for reprocessing of this type of endoscope.

Protein

A positive protein pad indicates there is $\geq 30$ ug/ml of protein remaining in the biopsy/suction channel sample. Benchmark studies indicate that with adequate cleaning and rinsing, <30 ug/ml of protein should remain in the scope sample.

Blood (Haemoglobin)

A positive blood pad indicates there is $\geq 10$ ug/ml of blood or haemoglobin remaining in the biopsy/suction channel sample. Benchmark studies indicate that with adequate cleaning and rinsing <10 ug/ml of blood should remain in the scope sample.

Leukocyte Esterase

A positive leukocyte esterase pad indicates that there are white blood cells present in the biopsy/suction channel OR that there is residual enzymatic detergent remaining. Benchmark studies indicate that with adequate cleaning and rinsing there should be no detectable leukocyte esterase reaction in the scope sample.

Glucose

A positive glucose pad indicates that there is >50 nmoles glucose present. Benchmark studies indicate that with adequate cleaning and rinsing there should be no detectable glucose remaining in the scope sample.

Quality Assurance Evaluations

The kit can also be used to:
1. assess if staff training for endoscope cleaning is adequate, or
2. to ensure that protocol changes (eg new detergent) do not detrimentally alter the in-house cleaning efficacy.

To perform this Quality Assurance Testing, you will need to obtain a separate bottle of the ATS. This ATS is a sterile test soil and is used to "soil" a flexible endoscope that will be used for quality assurance testing of either staff competency (re: endoscope cleaning) or protocol change validation (eg. New detergent or other protocol change being introduced).

Quality Assurance Procedure
1. Staff Competency Testing

Place the distal end of the flexible endoscope into a tube containing 10 mls of ATS.

Close the suction/air/water valves.

Attach the sample-collection tube to the biopsy port (FIG. 7) and draw up ATS into the suction channel until you can see it coming up the sample collection tube.

Allow excess ATS to drain out of the distal end of the suction/biopsy channel back into the ATS tube.

Allow the "soiled" endoscope to rest on the bench at room temperature for 30 minutes.

Ask the newly trained staff member to clean the soiled endoscope without any prompting from the trainer.

After cleaning is complete, take a sample from the suction/biopsy channel as described under the Test section of this brochure.

Any positive reactions indicate that the staff member has not yet achieved competency in the cleaning method, as no positive test pads should be detected if adequate cleaning has been performed.

2. Procedure Changes

Whenever an alteration to the existing reprocessing protocol is to be implemented, the changed protocol should be pre-tested before being implemented to ensure there is no detrimental effect on cleaning efficacy. Examples of procedure changes would include—new enzymatic detergent, different type of rinse water, alteration in method of brushing/rinsing, etc.

A clean flexible endoscope would be soiled as described under the staff competency testing. Cleaning with the altered protocol would be performed, then a scope sample collected. Testing of this scope sample should not show any positive reactions. If positive reactions are detected, the change of protocol needs to be reviewed and adjusted before it is implemented on patient-used endoscopes.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Abbott C F, Cockton J, Jones W. Science papers and discussions, resistance of crystalline substances to gas sterilization. J. Pharm. Pharmacol. 1956; 6:709–721.

Agerton T, Valway S, Gore B, et al. Transmission of a Highly Drug-Resistant Strain (Strain W1) of *Mycobacterium tuberculosis*. Community Outbreak and Nosocomial Transmission via a Contaminated Bronchoscopes. JAMA 1997;278:1073–1077.

Alfa M J, Degagne P, Olson N. Worst-case soiling levels for patient-used flexible endoscopes before and after cleaning. AJIC 1999 (in press).

Alfa M J, Sitter D L. In-hospital evaluation of contamination of duodenoscopes: a quantitative assessment of the effect of drying. Hosp Infect Soc 1991;19:89–98.

Alfa M J, Sitter D L. In-hospital evaluation of orthophthalaldehyde as a high level disinfectant for flexible endoscopes. J Hosp Infect 1994;26:15–26.

Alfa M J, DeGagne P, Olson N. Bacterial Killing Ability of 10% Ethylene Oxide Plus 90% Hydrochlorofluorocarbon Sterilizing Gas. Infect Control Hosp Epidem 1997;18(9): 641–645.

Alfa M J, DeGagne P, Olson N, Hizon R. Comparison of Liquid Chemical Sterilization using Peracetic Acid to Ethylene Oxide Sterilization for Long Narrow Lumens. Am J Infect Control 1998 (in press).

Alfa M J, DeGagne P, Olson N. (1999) Worst-Case Soiling Levels for Patient-Used Flexible Endoscopes Before and After Cleaning. American Journal of Infection Control (in press).

Alfa M J, DeGagne P, Olson N, Puchalski T. Comparison of Ion Plasma, Vaporized Hydrogen Peroxide, and 100% Ethylene Oxide Sterilizers to the 12/88 Ethylene Oxide Gas Sterilizer. Infect Control Hosp Epidem 1996;17(2): 92–100.

Allen J I, O'Connor-Allen M, Olson M. M. Pseudomonas Infection of the Biliary System Resulting From Usage of a Contaminated Endoscope. Gastroenterol 1987;92:759–63.

American Public Health Association Recommendation 9417: Establishment of clearly defined performance standards for between-patient processing of reusable endoscopic instruments and accesories. Am. J. Public Health 1995 85:449.

Baker K, McCullagh L. Comparison of actual and recommended ENT endoscope disinfection practices, by geographical regions in the United States. ORL-Head and Neck Nursing 1997 15:14–17.

Bronowicki J P, Venard V, Botte Christine, et al. Patient-To-Patient Transmission of Hepatitis C Virus During Colonoscopy. NEJM 1997;337(4):237–240.

Chan-Myers H, McAlister D, Antonoplos P. Natural bioburden levels detected on rigid lumened medical devices before and after cleaning. AJIC 1997; 25(6):471–476.

Cleaning and disinfection of equipment for gastrointestinal endoscopy. Report of a Working Party of the British Society of Gastroenterology Endoscopy Committee. GUT 1998 42:585–593.

Designing, testing, and labeling reusable medical devices for reprocessing in health care facililities: A guide for device manufacturers. AAMI TIR 1995;12:1–53.

Designing, Testing and Labeling Reusable Medical Devices for Reprocessing in Health Care Facilities: A Guide for Device Manufacturers. AAMI TIR No. 12 1994.

Descoutaux J C, Poulin E C, Julien M, Guidoin R. Residual Organic Debris on Processed Surgical Instruments. AORN J 1995;62(1):23–26.

DiMarino A J, et al Position Statement: Reprocessing of flexible gastrointestinal endoscopes 1996 43:540–546.

Favero M S, Pugliese G. Infections transmitted by endoscopy: An international problem. Am J Infect Control 1996;24:343–5.

Fujita N., Harada Y A new method to validating cleaning of internal channels of flexible gastro-endoscopes, using a dye of Amido Black. J. Hosp. Infection 1998 Suplement A, Vol 40, P.9.4.2

Guidance on the content and format of premarket notification 510(k) submissions for liquid chemical sterilants and high level disinfectants. Infection Control Devices Branch Division of Dental, Infection Control and General Hospital Devices Office of Device Evaluation Center for Devices and Radiological Health. U.S. Department of Health and Human Services Food and Drug Administration Center for Devices and Radiological Health. Final Revised Draft released for comment on Dec. 12, 1997.

Hanson P J V, et al. Elimination of high titre HIV from fiber optic endoscopes. Gut 1990;81:657–659.

Jacobs P T, Jenn-Hann W, Gorham R A, Roberts C G. Cleaning: Principles, Methods and Benefits. In: Rutala W. (Editor). Disinfection, Sterilization and Antisepsis in Health Care. Association for Professionals in Infection Control and Epidemiology, Washington D.C., and Polyscience Publications Inc. Champlain N.Y. (Publishers) 1998: pages 65–181.

Kruger S. Testing the cleaning efficacy in decontamination equipment. Zentr Steril 1997 5:333–344

Liu D, Lau Y L, Chau Y K, Pacepavicius G. Simple Technique for Estimation of Biofilm Accumulation. Bull Environ Contam Toxicol 1994;53:913–918.

Martin M A, Reichelderfer M. APIC guideline for infection prevention and control in flexible endoscopy. Am J Infect Control 1994;22:19–38.

McCracken J E. Endoscopy reveals debris, fluid, and damage in patient-ready GI endoscopes. Infect Control Steriliz Tech 1995;1(6):32–43.

Method to Determine Efficacy of Cleaning Techniques for Reusable GI Endoscopes and Related Medical Instruments. (Simulated Use Test). Version 4.0, March 1991; 1–12.

Michele T M, Cronin W A, Graham N M H, et al. Transmission of *Mycobacterium tuberculosis* by a Fiberoptic Bronchoscope. Identification by DNA Fingerprinting. JAMA 1997;278(13):1093–1095.

Nystrom B. Disinfection of surgical instruments. J Hosp Infect 1981;2:363–8.

Pflug I J, Holcomb R G. Principles of thermal destruction of microorganisms. In: Block S eds. Disinfection, Sterilization and Preservation. Philadelphia: Lea & Febiger. 4th Edition, 1991:85–128.

Pineau L, Roques C, Luc J, Michel G. Automatic Washer Disinfector for Flexible Endoscopes: A New Evaluation Process. Endoscopy 1997;29:372–379.

Roth K, Heeg P, Reichl R, Buess G F Validation of the Cleaning Stage. Presented at the Fifth World Congress on CSR on May 1999, Orlando Fla.

Royce A, Bowler C. Ethylene oxide sterilization—some experiences and some practical limitations. J. Pharm. Pharmacol. 1961; 87t–94t.

Rutala W A, Gergen M F, Jones J F, Weber D J. Levels of microbial contamination on surgical instruments. AJIC 1998; 26(2):143–145.

Rutala W. A. APIC guideline for selection and use of disinfectants, APIC guidelines for infection control practice. AJIC 1996 4:313–342.

Spach D H, Silverstein F E, Stamm W E. Transmission of Infection by Gastrointestinal Endoscopy and Bronchoscopy. Ann Intern Med 1993:118:117–128.

Tucker R C, Lestini B J, Marchant R E. Surface Analysis of Clinically Used Expanded PTFE Endoscopic Tubing Treated By the STERIS PROCESS. ASAIO J 1996;42(4): 306–313.

Verjat D., Prognon P, Darbord J C. Fluorescence-Assay on Traces of Protein on Re-Usable Medical Devices: Cleaning Efficiency. International Journal of Pharmaceutics. 1999 179:267–271.

Vesley D, Norlien K G, Nelson B, Ott B, Streifel A J. Significant factors in the disinfection and sterilization of flexible endoscopes. Am J Infect Control 1992;20(6): 291–300.

West A B, Kuan S-F, Bennick M, Lagarde S. Glutaraldehyde colitis following endoscopy: Clinical and pathological features and investigation of an outbreak. Gastroenterology 1995 108:1250–1255.

TABLE 1

Endoscopes Evaluated

| Endoscope: | Endoscope Type*: | Endoscope suction channel dimensions+: | Procedure: | Length of procedure (minutes) |
|---|---|---|---|---|
| Colonoscopes: | | | | |
| C-Pre1** | EVIS-video CF-100L | 1910 mm × 3.2 mm | Multiple biopsies | 20 |
| C-Pre2 | EVIS-video CF-100L | 1910 mm × 3.2 mm | Polypectomy | 32 |
| C-Pre3 | EVIS-video CF-100L | 1910 mm × 3.2 mm | Biopsies | 15 |
| C-Pre4 | EVIS-video CF-100L | 1910 mm × 3.2 mm | Biopsies | 33 |
| C-Pre5 | EVIS-video CF-100L | 1910 mm × 3.2 mm | Cautery polyps/Biopsy | 25 |
| C-Pre6 | EVIS-video CF-100L | 1910 mm × 3.2 mm | Polypectomy | 55 |
| C-Pre7 | EVIS-video CF-100L | 1910 mm × 3.2 mm | Polypectomy | 28 |
| C-Pre8 | EVIS-video CF-100L | 1910 mm × 3.2 mm | Visualization | 9 |
| C-Pre9 | EVIS-video CF-100L | 1910 mm × 3.2 mm | Visualization | 26 |
| C-Pre10 | EVIS-video CF-100L | 1910 mm × 3.2 mm | Visualization | 20 |
| C-Pre11 | EVIS-video CF-100L | 1910 mm × 3.2 mm | Visualization | NA |
| C-Post1** | EVIS-video CF-100L | 1910 mm × 3.2 mm | Polypectomy | 30 |
| C-Post2 | EVIS-video CF-100L | 1910 mm × 3.2 mm | Biopsy | 25 |
| C-Post3 | EVIS-video CF-100L | 1910 mm × 3.2 mm | Visualization | 25 |
| C-Post4 | EVIS-video CF-100L | 1910 mm × 3.2 mm | Polypectomy | 20 |
| C-Post5 | EVIS-video CF-100L | 1910 mm × 3.2 mm | Visualization | 27 |
| C-Post6 | EVIS-video CF-100L | 1910 mm × 3.2 mm | Sigmoidoscopy | 15 |
| C-Post7 | EVIS-video CF-100L | 1910 mm × 3.2 mm | Visualization | 18 |
| C-Post8 | EVIS-video CF-100L | 1910 mm × 3.2 mm | Visualization | 22 |
| C-Post9 | CF-20L (non-video) | 1940 mm × 3.2 mm | Biopsy | 15 |
| C-Post10 | EVIS-video CF-100L | 1910 mm × 3.2 mm | Polypectomy | 39 |
| Duodenoscopes: | | | | |
| D-Pre1 | JF-1T20 | 1510 mm × 3.2 mm | Gastroscopy | 30 |
| D-Pre2 | TJF-130 video | 1490 mm × 3.2 mm | Balloon manipulation | 16 |
| D-Pre3 | TJF-130 video | 1490 mm × 3.2 mm | Gastroscopy | 12 |
| D-Pre4 | TJF-130 video | 1490 mm × 3.2 mm | Stint replaced | 28 |
| D-Pre5 | JF-IT10 | 1510 mm × 2.8 mm | Stint inserted | 20 |
| D-Pre6 | TJF-130 video | 1490 mm × 3.2 mm | Gastroscopy | 40 |
| D-Pre7 | JF-IT10 | 1510 mm × 2.8 mm | Gastroscopy | 17 |
| D-Pre8 | TJF-130 video | 1490 mm × 3.2 mm | Spincterotomy and balloon manip. | 28 |
| D-Pre9 | TJF-130 video | 1490 mm × 3.2 mm | Stint inserted | 30 |
| D-Pre10 | TJF-130 video | 1490 mm × 3.2 mm | Gastroscopy | 45 |
| D-Post1 | TJF-130 video | 1490 mm × 3.2 mm | Visualization | 16 |
| D-Post2 | JF-IT10 | 1510 mm × 2.8 mm | Visualization | 70 |
| D-Post3 | TJF-130 video | 1490 mm × 3.2 mm | Biopsy | 25 |
| D-Post4 | TJF-130 video | 1490 mm × 3.2 mm | Visualization | 55 |
| D-Post5 | TJF-130 video | 1490 mm × 3.2 mm | Visualization | 30 |
| D-Post6 | TJF-130 video | 1490 mm × 3.2 mm | Spincterotomy and balloon manip. | 58 |
| D-Post7 | TJF-130 video | 1490 mm × 3.2 mm | Visualization | 25 |
| D-Post8 | JF-IT10 | 1510 mm × 2.8 mm | Visualization | 28 |
| D-Post9 | TJF-130 video | 1490 mm × 3.2 mm | Balloon manip. | 35 |
| D-Post10 | TJF-130 video | 1490 mm × 3.2 mm | Balloon manip. | 35 |
| Bronchoscopes | | | | |
| B-Pre1 | BFP30D | 660 mm × 2.2 mm | Microbiology cultures | 65 |
| B-Pre2 | BFP20D | 660 mm × 2.2 mm | Microbiology cultures | 60 |
| B-Pre3 | BFP20D | 660 mm × 2.2 mm | Microbiology cultures | 45 |
| B-Pre4 | BFP20D | 660 mm × 2.2 mm | Microbiology cultures | 45 |
| B-Pre5 | BFP20D | 660 mm × 2.2 mm | Microbiology cultures | 30 |
| B-Pre6 | BFP30D | 660 mm × 2.2 mm | Microbiology cultures | 67 |
| B-Pre7 | BFP20D | 660 mm × 2.2 mm | Microbiology cultures | 18 |
| B-Pre8 | BFP30D | 660 mm × 2.2 mm | Microbiology cultures | 26 |
| B-Pre9 | BFP20D | 660 mm × 2.2 mm | Microbiology cultures | 20 |
| B-Pre10 | BFP20D | 660 mm × 2.2 mm | Microbiology cultures | 10 |
| B-Post1 | BFP20D | 660 mm × 2.2 mm | Surgery, cytology | 30 |
| B-Post2 | BFP20D | 660 mm × 2.2 mm | Microbiology cultures | 33 |
| B-Post3 | BFP20D | 660 mm × 2.2 mm | Microbiology cultures | 8 |
| B-Post4 | BFP30D | 660 mm × 2.2 mm | Surgery, Cytology | 27 |
| B-Post5 | BFP20D | 660 mm × 2.2 mm | Microbiology cultures | 37 |
| B-Post6 | BFP30D | 660 mm × 2.2 mm | Microbiology cultures | 20 |
| B-Post7 | BFP30D | 660 mm × 2.2 mm | Microbiology cultures | 25 |
| B-Post8 | BFP30D | 660 mm × 2.2 mm | Microbiology cultures | 55 |
| B-Post9 | BFP20D | 660 mm × 2.2 mm | Microbiology cultures | 30 |
| B-Post10 | BFP20D | 660 mm × 2.2 mm | Microbiology cultures | 75 |

*All flexible endoscopes were manufactured by Olympus Corp. (Lake Success, N.Y., USA)
+The internal suction channel dimensions were used to determine the cm² for each endoscope and all quantitative data is presented as amount/device as well as amount/cm²
**Al PRE samples were taken directly after patient-use (no rinsing) and all POST samples were taken after routine cleaning (see materials and methods) but before high level disinfection.

TABLE 2

SOIL IN PATIENT-USED ENDOSCOPES PRIOR TO CLEANING (WORST-CASE SOIL)*

A. Soil levels detected per suction channel surface area of endoscope:

| Endoscope | Hemoglobin $\mu g/cm^2$ | Bilirubin nmoles/cm$^2$ | Protein $\mu g/cm^2$ | Sodium ion $\mu mole/cm^2$ | Endotoxin EU/cm$^2$ | Carbohydrate $\mu g/cm^2$ | Viable Bacteria $Log_{10}$ cfu/cm$^2$ |
|---|---|---|---|---|---|---|---|
| Bronchoscope | | | | | | | |
| Average: | 13.37 | Not detected | 28.26 | 2.56 | 23.13 | 0.78 | 4.19 |
| Median: | 6.58 | in any sample | 10.85 | 1.64 | 2.14 | 0.00 | 4.06 |
| Range: | (0–85.49) | | (1.75–95.80) | (0.87–7.45) | (0.25–141.51) | (0–3.27) | (2.35–5.64) |
| Duodenoscope | | | | | | | |
| Average: | 2.00 | 0.29 | 11.32 | 0.73 | 3.36 | 1.03 | 3.45 |
| Median: | 0.00 | 0.03 | 9.15 | 0.57 | 0.47 | 0.96 | 3.81 |
| Range: | (0–12.68) | (0–2.24) | (1.80–29.44) | (0.15–2.14) | (0.1–17.84) | (0–2.17) | (0–5.29) |
| Colonoscope | | | | | | | |
| Average: | 6.44 | 1.63 | 37.05 | 0.71 | 911.38 | 4.69 | 4.93 |
| Median: | 0.52 | 0.052 | 16.93 | 0.52 | 10.39 | 1.38 | 4.75 |
| Range: | (0–34.89) | (0–15.57) | (1.77–115.51) | (0.21–2.76) | (0.47–9852.83) | (0–29.11) | (3.43–7.16) |

*Average and Median soil amount/cm$^2$ for 10 of each type of endoscope (range of soil concentrations). The inner suction channel dimensions for all endoscopes used is given in Table 1 (surface area calculated as length × circumference of inner suction channel).

B. Soil Levels Detected per device+

| Endoscope | Hemoglobin $\mu g$/device | Bilirubin nmoles/device | Protein $\mu g$/device | Sodium ion $\mu mole$/device | Endotoxin EU/device | Carbohydrate $\mu g$/device | Viable Bacteria $Log_{10}$ cfu/device |
|---|---|---|---|---|---|---|---|
| Bronchoscope | | | | | | | |
| Average: | 610.00 | Not detected | 1290.00 | 117.00 | 1054.87 | 35.53 | 6.76 |
| Median: | 300.00 | in any sample | 500.00 | 75.00 | 97.58 | 0.00 | 6.08 |
| Range: | (0–3900.00) | | (220–4370.00) | (40.00–340.00) | (11.34–6455.00) | (0–149.20) | (4.01–7.29) |
| Duodenoscope | | | | | | | |
| Average: | 300.00 | 45.00 | 1680.00 | 109.00 | 499.37 | 151.25 | 6.84 |
| Median: | 0.00 | 5.00 | 1280.00 | 85.00 | 70.91 | 143.30 | 6.14 |
| Range: | (0–1900.00) | (0–340.00) | (360–4410.00) | (10.00–320.00) | (6.28–2708.62) | (0–288.10) | (0–7.45) |
| Colonoscope | | | | | | | |
| Average: | 1240.00 | 312.73 | 7110.00 | 135.45 | 174997.96 | 990.73 | 8.46 |
| Median: | 100.00 | 10.00 | 3250.00 | 100.00 | 1994.62 | 379.25 | 7.03 |
| Range: | (0–6700.00) | (0–2990) | (340–22,180) | (20–530.00) | (89.24–1891880.71) | (0–5590.00) | (5.72–9.45) |

*Average and Median soil level per device for 10 of each type of endoscope (range of soil concentrations). Data reported as amount per 10 mls sample taken from each device.
+"Device" is the flexible endoscope suction channel.

TABLE 3

SOIL IN PATIENT-USED ENDOSCOPES AFTER CLEANING BUT PRIOR TO HIGH-LEVEL DISINFECTION (WORST-CASE SOIL POST-CLEANING)*

A Soil levels detected per suction channel surface area of device

| Endoscope | Hemoglobin $\mu g/cm^2$ | Bilirubin nmoles/cm$^2$ | Protein $\mu g/cm^2$ | Sodium ion $\mu mole/cm^2$ | Endotoxin EU/cm$^2$ | Carbohydrate $\mu g/cm^2$ | Viable Bacteria $Log_{10}$ cfu/cm$^2$ |
|---|---|---|---|---|---|---|---|
| Bronchoscope | | | | | | | |
| Average: | 2.19 | <LD | 6.12 | 0.94 | 4.55 | <LD | 2.89 |
| Median: | 2.19 | | 6.36 | 0.77 | 2.23 | | 2.79 |
| Range: | (0–4.4) | | (3.51–8.55) | (0.77–1.54) | (0.27–19.61) | | (2.17–4.05) |
| Duodenoscope | | | | | | | |
| Average: | <LD | <LD | 1.17 | 0.08 | 0.02 | 1.79 | 2.22 |
| Median: | | | 1.20 | 0.07 | 0.002 | 1.18 | 1.94 |
| Range: | | | (0.20–2.26) | (0.07–0.13) | (0.001–0.06) | (0–5.28) | (1.49–3.17) |
| Colonoscope | | | | | | | |
| Average: | <LD | <LD | 0.87 | 0.05 | 0.07 | <LD | 1.82 |
| Median: | | | 0.96 | 0.05 | 0.03 | | 1.82 |
| Range: | | | (0.52–1.19) | (0.05–0.052) | (0.005–0.46) | | (0.89–2.33) |

*Average and Median soil amount/cm$^2$ for 10 of each type of endoscope (range of soil concentrations). The inner suction channel dimensions for all endoscopes used is given in Table 1 (surface area calculated as length × circumference of inner suction channel).

TABLE 3-continued

SOIL IN PATIENT-USED ENDOSCOPES AFTER CLEANING BUT PRIOR TO HIGH-LEVEL DISINFECTION (WORST-CASE SOIL POST-CLEANING)*

3B. Soil Detected per Device[+]

| Endoscope | Hemoglobin μg/device | Bilirubin nmoles/device | Protein μg/device | Sodium ion μmole/device | Endotoxin EU/device | Carbohydrate μg/device | Viable Bacteria $Log_{10}$ cfu/device |
|---|---|---|---|---|---|---|---|
| Bronchoscope | | | | | | | |
| Average: | 100.00 | <LD | 280.00 | 43.00 | 207.49 | <LD | 4.91 |
| Median: | 100.00 | | 290.00 | 35.00 | 101.88 | | 4.45 |
| Range: | (0–200.0) | | (160–390.00) | (30–70.00) | (12.45–894.40) | | (3.83–5.71) |
| Duodenoscope | | | | | | | |
| Average: | <LD | <LD | 170.00 | 12.00 | 2.49 | 264.19 | 4.79 |
| Median: | | | 180.00 | 10.00 | 0.34 | 164.70 | 4.10 |
| Range: | | | (50.00–300.00) | (10.00–20.00) | (0.10–9.61) | (0–791.80) | (3.67–5.34) |
| Colonoscope | | | | | | | |
| Average: | <LD | <LD | 170.00 | 10.00 | 13.46 | <LD | 4.27 |
| Median: | | | 190.00 | 10.00 | 5.70 | | 4.10 |
| Range: | | | (10.00–230.00) | (10.00–10.00) | (0.96–87.90) | | (3.17–4.61) |

* Average and Median soil level per device for 10 of each type of endoscope (range of soil concentrations). Data presented as amount per 10 mls sample taken from each device.
[+]"Device" is the flexible endoscope suction channel.

TABLE 4

Composition of average and worst-case soil from patient-used endoscopes

| | Average Soil:* | Worst-case Soil |
|---|---|---|
| Hemoglobin | | |
| $μg/cm^2$ | 7.39 | 86 |
| μg/ml** | 254 | 670 |
| μg/device+ | 2540 | 6700 |
| Bilirubin*** | | |
| $nmoles/cm^2$ | 0.96 | 16 |
| nmoles/ml | 17.9 | 299 |
| nmoles/device | 179 | 2990 |
| Protein | | |
| $μg/cm^2$ | 0.71 | 115 |
| μg/ml | 25.53 | 2200 |
| μg/device | 255.3 | 22000 |
| Sodium ion++ | | |
| $μmole/cm^2$ | 1.33 | 7.5 |
| μmole/ml | 12.0 | 34 |
| μmole/device | 120 | 340 |
| Carbohydrate | | |
| $μg/cm^2$ | 2.2 | 29 |
| μg/ml | 39.2 | 559 |
| μg/device | 393 | 5590 |
| Endotoxin | | |
| $EU/cm^2$ | 312.5 | 9900 |
| EU/ml | 5884 | 189188 |
| EU/device | 58840 | 1891880 |

*The average of the 10 PRE measurements for all three types of endoscopes.
**The average concentration per ml does not compensate for differences in suction channel lengths of the various endoscopes, whereas amount/$cm^2$ does.
***Bilirubin data was for colonoscope and duodenoscope PRE samples only, as none was detected in any of the 10 PRE bronchoscopes tested.
+"Device" is the flexible endoscope suction channel.
++The sodium ion concentration of normal saline would be 5.78 μmole/$cm^2$ (156 μmole/ml) based on inoculation of 10 μl onto a carrier. The surface area used for this calculation was 0.27 $cm^2$ which was the surface area determined when 10 μl was inoculated onto a PVC coupon.

TABLE 5

Composition determinations for various Test soil formulations compared to Patient-used soil levels

| Test Soil Type: | Hg $μg/cm^{2*}$ (μg/ml) | Bilirubin $nmoles/cm^2$ (nmole/ml) | Protein $μg/cm^2$ (μg/ml) | Sodium $μmole/cm^2$ (μmole/ml) | Chloride $μmole/cm^2$ (μmole/ml) | Carbohydrate $μg/cm^{2+}$ (μg/ml) | Endotoxin $EU/cm^2$ (EU/ml) |
|---|---|---|---|---|---|---|---|
| Edinburgh soil | 3,278 (88,500) | 0 | 2,211 (59,700) | 3.7 (100) | 2.59 (70) | 37.7 (1019)[++] | 0 |
| 100% Blood | 6556 | 0 | 2592 () | 5.78 (156) | 5.48 (148) | 399 | 0 |
| 10% FBS | 0 | 0 | 151 (4080) | 0.59 (16) | 0.70 (19) | 18.7 (505) | 0 |
| Normal Saline | 0 | 0 | 0.11 (3.0) | 5.78 (156) | 5.48 (148) | <LD | 0 |
| ATS-B | 30 (820) | 0 | 157 (4235) | 5.1 (139) | 4.07 (110) | 72.2 (1949) | 923 (24,943) |

TABLE 5-continued

Composition determinations for various Test soil formulations compared to Patient-used soil levels

| Test Soil Type: | Hg $\mu g/cm^2{}^*$ ($\mu g/ml$) | Bilirubin nmoles/cm$^2$ (nmole/ml) | Protein $\mu g/cm^2$ ($\mu g/ml$) | Sodium $\mu mole/cm^2$ ($\mu mole/ml$) | Chloride $\mu mole/cm^2$ ($\mu mole/ml$) | Carbohydrate $\mu g/cm^{2+}$ ($\mu g/ml$) | Endotoxin EU/cm$^2$ (EU/ml) |
|---|---|---|---|---|---|---|---|
| ATS-GI | 32 (860) | 0.6 (15) | 186 (5035) | 6.7 (181) | 5.14 (140) | 152.5 (4118) | 152.5 (8,107) |
| Worst-case Soil (Patient-used scope) | 86 (670) | 16** (299) | 115 (2,200) | 7.5 (34) | 6.36 (28.0) | 29 (559) | 9,900 (189,188) |
| Average Soil (Patient-used scope) | 7.39 (254) | 0.96** (17.9) | 25.53 (252) | 1.33 (12.0) | 1.33 (12.86) | 2.2 (39.2) | 312.5 (5,884) |

*The amount/cm$^2$ was based on inoculation of 10 $\mu l$ of the test soil onto a test carrier. The surface area used for these calculations was 0.27 cm$^2$ which is the surface area determined for 10 $\mu l$ inoculated onto PVC coupons.
**Bilirubin data was for colonoscopes and duodenoscope samples, as none was found in the 20 bronchoscopes tested.
+Aseptizyme detergent (at working strength) contained 562.2 $\mu g/ml$ carbohydrate
++The carbohydrate content of Edinburgh soil was primarily due to the egg component (76%), with blood contributing less (24%).

TABLE 6

CHEMISTRY AND DIP-STRIP COMPARISON FROM PRE AND POST CLEANED PATIENT-USED COLONOSCOPES

CHEMISTRY ANALYSIS RESULTS ON SCOPE SAMPLES

| SAMPLE CODE #: | PLASMA Hg (g/L): | SERUM BILIRUBIN ($\mu$moles/L): | URINE PROTEIN (g/L): | BIORAD MICRO-ASSAY PROTEIN (g/L): | PROTEIN PROZONE EFFECT? | URINE SODIUM (mmoL/L): | URINE POTASSIUM (mmoL/L): | URINE CHLORINE (mmoL/L): | LAL RESULTS (EU/mL): | CARBO-HYDRATE ($\mu$g/mL): |
|---|---|---|---|---|---|---|---|---|---|---|
| C-PRE 1 | −0.04 | 0 | 0.034 | 0.052 | NO | 4 | 0.2 | 17 | 126.361 | 13.22 |
| C-PRE 2 | −0.02 | 9 | 0.264 | | NO | 21 | 6.6 | 15 | 199.462 | 134.90 |
| C-PRE 3 | 0.01 | 7 | 0.264 | | NO | 53 | 5.7 | 15 | 1402.806 | 49.27 |
| C-PRE 4 | −0.03 | 1 | 0.160 | | NO | 8 | 2.9 | 12 | 107.529 | 54.90 |
| C-PRE 5 | −0.03 | 0 | 0.166 | | NO | 4 | 3.3 | 12 | 37.866 | 22.12 |
| C-PRE 6 | 0.02 | 1 | 0.765 | | NO | 10 | 7.7 | 14 | 8.942 | 0 |
| C-PRE 7 | −0.04 | 1 | 0.044 | 0.034 | NO | 7 | 1.0 | 12 | 12.183 | 5.437 |
| C-PRE 8 | 0.06 | 1 | 0.366 | | NO | 2 | 1.7 | 11 | 726.500 | 26.580 |
| C-PRE 9 | 0.22 | 6 | 1.496 | | NO | 12 | 11.5 | 11 | 347.405 | 125.30 |
| C-PRE 10 | 0.67 | 299 | 1.986 | | NO-HIGH (1:3) | 13 | 6.7 | 9 | 340.648 | 559 |
| C-PRE 11 | 0.38 | 19 | 2.218 | | NO-HIGH (1:3) | 15 | 13.6 | 5 | 189188.071 | N/A |
| C-POST 1 | −0.05 | 0 | 0.013 | 0.001 | YES (×2) | 1 | 0.1 | 18 | 0.235 | 0 |
| C-POST 2 | −0.04 | 0 | 0.023 | 0.006 | YES | 1 | 0.4 | 13 | 0.692 | 0 |
| C-POST 3 | −0.04 | 0 | 0.021 | 0.007 | YES | 1 | 0.2 | 12 | 0.552 | 0 |
| C-POST 4 | −0.04 | 0 | 0.020 | 0.002 | NO | 1 | 0.1 | 11 | 8.790 | 0 |
| C-POST 5 | −0.04 | 0 | 0.016 | 0.0008 | YES | 1 | 0.1 | 10 | 0.165 | 0 |
| C-POST 6 | −0.04 | 0 | 0.014 | 0.002 | YES | 1 | 0.1 | 11 | 1.146 | 0 |
| C-POST 7 | −0.04 | 0 | 0.018 | 0.0030 | NO | 1 | 0.1 | 10 | 0.096 | 0 |
| C-POST 8 | −0.04 | 0 | 0.023 | 0.002 | NO | 1 | 0.1 | 11 | 0.163 | 0 |
| C-POST 9 | −0.03 | 0 | 0.019 | 0.003 | NO | 1 | 0.1 | 10 | 1.030 | 0 |
| C-POST 10 | −0.04 | 0 | 0.001 | 0.009 | YES | 1 | 0.1 | 10 | 0.587 | 0 |

CHEMSTRIP DIPSTICK ANALYSIS

| SAMPLE CODE #: | pH | LEUKOCYTES (#/uL): | NITRITE | PROTEIN (g/L): | GLUCOSE (mmol/L): | KETONES | UROBILINOGEN ($\mu$moles/L): | BILIRUBIN ($\mu$moles/L): | BLOOD (ery/uL): |
|---|---|---|---|---|---|---|---|---|---|
| C-PRE 1 | 5.0 | 500 | neg | 0.15 | norm | neg | norm | neg | 250 |
| C-PRE 2 | 7.0 | 500 | neg | 0.15 | norm | neg | norm | neg | 250 |
| C-PRE 3 | 7.0 | 500 | neg | 0.30 | norm | neg | norm | neg | 250 |
| C-PRE 4 | 7.0 | 25 | neg | 0.15 | norm | neg | norm | neg | 50 |
| C-PRE 5 | 7.0 | 100 | neg | 0.30 | norm | neg | norm | neg | 250 |
| C-PRE 6 | 8.0 | 500 | neg | 1.00 | norm | neg | norm | neg | 250 |
| C-PRE 7 | 7.0 | 100 | neg | neg | norm | neg | norm | neg | 250 |
| C-PRE 8 | 7.0 | 500 | neg | 0.30 | norm | neg | norm | neg | 50 |
| C-PRE 9 | 7.0 | 500 | pos | 1.00 | norm | neg | norm | 17 | 150 |
| C-PRE 10 | 7.0 | 500 | pos | 1.00 | norm | neg | 17 | 100 | 150 |
| C-PRE 11 | | | | | | | | | |
| C-POST 1 | 5.0 | neg | neg | neg | norm | neg | norm | neg | neg |
| C-POST 2 | 7.0 | neg | neg | neg | norm | neg | norm | neg | neg |
| C-POST 3 | 7.0 | neg | neg | neg | norm | neg | norm | neg | neg |

TABLE 6-continued

CHEMISTRY AND DIP-STRIP COMPARISON FROM PRE AND POST CLEANED PATIENT-USED COLONOSCOPES

| | | | | | | | | | |
|---|---|---|---|---|---|---|---|---|---|
| C-POST 4 | 6.5 | neg | neg | neg | norm | neg | norm | neg | neg |
| C-POST 5 | 5.0 | neg | neg | neg | norm | neg | norm | neg | neg |
| C-POST 6 | 6.5 | neg | neg | 0.15 | norm | neg | norm | neg | neg |
| C-POST 7 | 6.5 | neg | neg | neg | norm | neg | norm | neg | neg |
| C-POST 8 | 5.0 | neg | neg | neg | norm | neg | norm | neg | neg |
| C-POST 9 | 5.0 | neg | neg | neg | norm | neg | norm | neg | neg |
| C-POST 10 | 5.0 | neg | neg | neg | norm | neg | norm | neg | neg |

NORMAL URINE LEVELS:
BILIRUBIN = 2–20 μmoles/L
TOTAL PROTEIN =< 0.14 g/day
SODIUM = 10–300 mmoL/L
POTASSIUM = 1.0–140.0 mmoL/L
CHLORINE = 20–300 mmoL/L
NORMAL SERUM LEVELS:
BILIRUBIN = 2–20 μmoles/L
TOTAL PROTEIN = 60–80 g/L
SODIUM = 135–147 mmol/L
POTASSIUM = 3.5–5.0 mmol/L
CHLORINE = 97–106 mmol/L
PLASMA Hg =< 0.10 g/L
PLASMA glucose = 700–1050 μg/mL
*LEVELS OUTSIDE THIS WILL BE FLAGGED AS LOW (L) OR HIGH (H). AND WILL BE RECORDED AS "PANIC" ON THE PRINTOUT!
NOTE:
A BIORAD MICROASSAY FOR THE PROTEINS WAS PERFORMED ON THE 26 SAMPLES THAT HAD A URINE PROTEIN VALUE OF LESS THAN 0.100 g/L.
NOTE:
FOR THE LAL ASSAY (LIMULUS AMEBOCYTE LYSATE), AND CHEMISTRY ASSAYS, THE SAMPLES WERE SONICATED 5 MINUTES, THEN SPUN AT ~1700 RPM FOR 10 MINUTES BEFORE TESTING.

TABLE 7

CHEMISTRY AND DIP-STRIP COMPARISON FROM PRE AND POST CLEANED PATIENT-USED DUODENOSCOPES

CHEMISTRY ANALYSIS RESULTS ON SCOPE SAMPLES

| SAMPLE CODE #: | PLASMA Hg (g/L): | SERUM BILIRUBIN (μmoles/L): | URINE PROTEIN (g/L): | BIORAD MICRO-ASSAY PROTEIN (g/L): | PROTEIN PROZONE EFFECT? | URINE SODIUM (mmoL/L): | URINE POTASSIUM (mmoL/L): | URINE CHLORINE (mmoL/L): | LAL RESULTS (EU/mL): | CARBO-HYDRATE (μg/mL): |
|---|---|---|---|---|---|---|---|---|---|---|
| D-PRE 1 | 0.00 | 34 | 0.370 | | NO | 20 | 1.3 | 19 | 270.862 | 26.09 |
| D-PRE 2 | 0.11 | 1 | 0.254 | | NO | 8 | 0.6 | 16 | 144.391 | 15.94 |
| D-PRE 3 | −0.04 | 0 | 0.063 | 0.037 | NO | 7 | 0.9 | 16 | 1.057 | 11.50 |
| D-PRE 4 | 0.19 | 1 | 0.441 | | NO | 32 | 1.0 | 28 | 8.005 | 25.67 |
| D-PRE 5 | −0.05 | 0 | 0.028 | 0.005 | YES (×2) | 2 | 0.2 | 14 | 34.115 | 0 |
| D-PRE 6 | −0.02 | 8 | 0.106 | | NO | 9 | 0.4 | 13 | 3.385 | 12.72 |
| D-PRE 7 | −0.03 | 0 | 0.149 | | NO | 7 | 0.7 | 7 | 29.873 | 28.81 |
| D-PRE 8 | −0.03 | 0 | 0.204 | | NO | 11 | 0.7 | 17 | 0.880 | 20.22 |
| D-PRE 9 | −0.05 | 1 | 0.036 | 0.060 | YES (×2) | 12 | 0.7 | 18 | 6.176 | 10.30 |
| D-PRE 10 | −0.05 | 0 | 0.027 | 0.003 | YES (×2) | 1 | 0.1 | 13 | 0.628 | 0 |
| D-POST 1 | −0.04 | 0 | 0.010 | 0.0003 | YES | 1 | 0.1 | 10 | 0.055 | 63.83 |
| D-POST 2 | −0.04 | 0 | 0.014 | 0.001 | YES (×2) | 1 | 0.1 | 10 | 0.010 | 19.36 |
| D-POST 3 | −0.05 | 0 | 0.003 | 0.0003 | YES | 1 | 0.1 | 10 | 0.014 | 0 |
| D-POST 4 | −0.04 | 0 | 0.027 | 0.004 | YES | 1 | 0.1 | 10 | 0.042 | 6.223 |
| D-POST 5 | −0.04 | 0 | 0.016 | 0.0007 | NO | 1 | 0.1 | 10 | 0.026 | 13.58 |
| D-POST 6 | −0.04 | 0 | 0.023 | 0.001 | NO | 2 | 0.1 | 10 | 0.961 | 79.18 |
| D-POST 7 | −0.03 | 0 | 0.022 | 0.0009 | NO | 2 | 0.1 | 10 | 0.946 | 40.64 |
| D-POST 8 | −0.05 | 0 | 0.030 | 0.006 | YES | 1 | 0.1 | 10 | 0.405 | 10.97 |
| D-POST 9 | −0.05 | 0 | 0.020 | 0.0003 | NO | 1 | 0.1 | 10 | 0.008 | 6.144 |
| D-POST 10 | −0.04 | 0 | 0.005 | 0.0009 | YES (×2) | 1 | 0.1 | 10 | 0.021 | 24.26 |

CHEMSTRIP DIPSTICK ANALYSIS

| SAMPLE CODE #: | pH | LEUKOCYTES (#/uL): | NITRITE | PROTEIN (g/L): | GLUCOSE (mmol/L): | KETONES | UROBILINOGEN (μmoles/L): | BILIRUBIN (μmoles/L): | BLOOD (ery/uL): |
|---|---|---|---|---|---|---|---|---|---|
| D-PRE 1 | 7.0 | 500 | neg | 0.30 | norm | neg | norm | 100 | 250 |
| D-PRE 2 | 7.0 | 500 | neg | 1.00 | norm | neg | norm | neg | 250 |
| D-PRE 3 | 5.0 | neg | neg | neg | norm | neg | norm | neg | neg |
| D-PRE 4 | 8.0 | 500 | neg | 1.00 | norm | neg | norm | neg | 250 |
| D-PRE 5 | 5.0 | neg | neg | neg | norm | neg | norm | neg | 50 |
| D-PRE 6 | 7.0 | 100 | neg | 0.15 | norm | neg | norm | 17 | 250 |
| D-PRE 7 | 7.0 | 500 | neg | neg | norm | neg | norm | neg | 150 |
| D-PRE 8 | 6.5 | neg | neg | 0.30 | norm | neg | norm | neg | 250 |

TABLE 7-continued

CHEMISTRY AND DIP-STRIP COMPARISON FROM PRE AND POST CLEANED PATIENT-USED DUODENOSCOPES

| | | | | | | | | | |
|---|---|---|---|---|---|---|---|---|---|
| D-PRE 9 | 5.0 | neg | neg | neg | norm | neg | norm | neg | 250 |
| D-PRE 10 | 6.5 | neg | neg | neg | norm | neg | norm | neg | 10 |
| D-POST 1 | 5.0 | neg | neg | 0.15 | norm | neg | norm | neg | neg |
| D-POST 2 | 5.0 | neg | neg | neg | norm | neg | norm | neg | neg |
| D-POST 3 | 6.5 | neg | neg | neg | norm | neg | norm | neg | neg |
| D-POST 4 | 5.0 | neg | neg | neg | norm | neg | norm | neg | neg |
| D-POST 5 | 5.0 | neg | neg | neg | norm | neg | norm | neg | neg |
| D-POST 6 | 7.0 | neg | neg | 0.15 | norm | neg | norm | neg | neg |
| D-POST 7 | 5.0 | neg | neg | neg | norm | neg | norm | neg | neg |
| D-POST 8 | 5.0 | neg | neg | neg | norm | neg | norm | neg | neg |
| D-POST 9 | 5.0 | neg | neg | neg | norm | neg | norm | neg | neg |
| D-POST 10 | 5.0 | neg | neg | neg | norm | neg | norm | neg | neg |

NORMAL URINE LEVELS:
BILIRUBIN = 2–20 μmoles/L
TOTAL PROTEIN =< 0.14 g/day
SODIUM = 10–300 mmoL/L
POTASSIUM = 1.0–140.0 mmoL/L
CHLORINE = 20–300 mmoL/L
NORMAL SERUM LEVELS:
BILIRUBIN = 2–20 μmoles/L
TOTAL PROTEIN = 60–80 g/L
SODIUM = 135–147 mmol/L
POTASSIUM = 3.5–5.0 mmol/L
CHLORINE = 97–106 mmol/L
PLASMA Hg =< 0.10 g/L
PLASMA glucose = 700–1050 μg/mL

TABLE 8

CHEMISTRY AND DIP-STRIP COMPARISON FROM PRE AND POST CLEANED PATIENT-USED BRONCHOSCOPES

CHEMISTRY ANALYSIS RESULTS ON SCOPE SAMPLES

| SAMPLE CODE #: | PLASMA Hg (g/L): | SERUM BILIRUBIN (μmoles/L): | URINE PROTEIN (g/L): | BIORAD MICRO-ASSAY PROTEIN (g/L): | PROTEIN PROZONE EFFECT? | URINE SODIUM (mmoL/L): | URINE POTASSIUM (mmoL/L): | URINE CHLORINE (mmoL/L): | LAL RESULTS (EU/mL): | CARBO-HYDRATE (μg/mL): |
|---|---|---|---|---|---|---|---|---|---|---|
| B-PRE 1 | 0.00 | 0 | 0.061 | | NO | 7 | 0.4 | 7 | 4.090 | 0 |
| B-PRE 2 | 0.03 | 0 | 0.036 | | NO | 7 | 0.3 | 7 | 7.675 | 0 |
| B-PRE 3 | 0.03 | 0 | 0.437 | | NO | 14 | 1.5 | 13 | 16.80 | 9.369 |
| B-PRE 4 | 0.39 | 0 | 0.388 | | NO | 6 | 0.5 | 6 | 299.3 | 0 |
| B-PRE 5 | 0.03 | 0 | 0.155 | | NO | 7 | 0.4 | 6 | 61.20 | 11.24 |
| B-PRE 6 | 0.02 | 0 | 0.119 | | NO | 8 | 0.5 | 7 | 645.5 | 0 |
| B-PRE 7 | 0.04 | 0 | 0.038 | | NO | 34 | 0.2 | 29 | 2.683 | 0 |
| B-PRE 8 | 0.04 | 0 | 0.022 | | NO | 9 | 0.2 | 8 | 1.134 | 0 |
| B-PRE 9 | 0.01 | 0 | 0.008 | | NO | 4 | 0.2 | 4 | 11.84 | 14.92 |
| B-PRE 10 | 0.02 | 0 | 0.025 | | NO | 21 | 0.2 | 17 | 4.647 | 0 |
| B-POST 1 | 0.01 | 0 | 0.027 | | NO | 3 | 0.2 | 4 | 22.33 | 0 |
| B-POST 2 | 0.01 | 0 | 0.016 | | NO | 6 | 0.2 | 4 | 1.245 | 0 |
| B-POST 3 | 0.01 | 0 | 0.030 | | NO | 7 | 0.3 | 6 | 31.64 | 0 |
| B-POST 4 | 0.01 | 0 | 0.025 | | NO | 3 | 0.2 | 3 | 10.57 | 0 |
| B-POST 5 | 0.02 | 0 | 0.033 | | NO | 5 | 0.2 | 4 | 31.70 | 0 |
| B-POST 6 | 0.01 | 0 | 0.030 | | NO | 3 | 0.2 | 3 | 8.180 | 0 |
| B-POST 7 | 0.00 | 0 | 0.034 | | NO | 3 | 0.2 | 3 | 1.292 | 0 |
| B-POST 8 | 0.01 | 0 | 0.028 | | NO | 4 | 0.2 | 3 | 1.282 | 0 |
| B-POST 9 | 0.02 | 0 | 0.017 | | NO | 3 | 0.2 | 3 | 9.806 | 0 |
| B-POST 10 | 0.00 | 0 | 0.039 | | NO | 6 | 0.3 | 4 | 89.44 | 0 |

CHEMSTRIP DIPSTICK ANALYSIS

| SAMPLE CODE #: | pH | LEUKOCYTES (#/uL): | NITRITE | PROTEIN (g/L): | GLUCOSE (mmol/L): | KETONES | UROBILINOGEN (μmoles/L): | BILIRUBIN (μmoles/L): | BLOOD (ery/uL): |
|---|---|---|---|---|---|---|---|---|---|
| B-PRE 1 | 6.5 | 100 | neg | 0.15 | norm | neg | norm | neg | 250 |
| B-PRE 2 | 5.0 | neg | neg | neg | norm | neg | norm | neg | 250 |
| B-PRE 3 | 5.0 | neg | neg | 1.00 | norm | neg | norm | neg | 250 |
| B-PRE 4 | 7.0 | 25 | neg | 1.00 | norm | neg | norm | neg | 250 |
| B-PRE 5 | 5.0 | 500 | neg | 0.30 | norm | neg | norm | neg | 250 |
| B-PRE 6 | 5.0 | neg | neg | 0.30 | norm | neg | norm | neg | 250 |
| B-PRE 7 | 5.0 | neg | neg | 0.30 | norm | neg | norm | neg | 250 |
| B-PRE 8 | 6.5 | 25 | neg | neg | norm | neg | norm | neg | neg |
| B-PRE 9 | 6.5 | neg | neg | neg | norm | neg | norm | neg | 10 |

TABLE 8-continued

CHEMISTRY AND DIP-STRIP COMPARISON FROM PRE AND POST CLEANED PATIENT-USED BRONCHOSCOPES

| B-PRE 10 | 5.0 | neg | neg | neg | norm | neg | norm | neg | neg |
|---|---|---|---|---|---|---|---|---|---|
| B-POST 1 | 5.0 | 25 | neg | 0.15 | norm | neg | norm | neg | neg |
| B-POST 2 | 6.5 | 25 | neg | neg | norm | neg | norm | neg | 250 |
| B-POST 3 | 5.0 | 100 | neg | neg | norm | neg | norm | neg | neg |
| B-POST 4 | 5.0 | 25 | neg | neg | norm | neg | norm | neg | 10 |
| B-POST 5 | 6.5 | neg | neg | 0.15 | norm | neg | norm | neg | neg |
| B-POST 6 | 7.0 | neg | neg | 0.15 | norm | neg | norm | neg | neg |
| B-POST 7 | 6.5 | 25 | neg | 0.15 | norm | neg | norm | neg | 150 |
| B-POST 8 | 6.5 | 25 | neg | neg | norm | neg | norm | neg | neg |
| B-POST 9 | 7.0 | neg | neg | neg | norm | neg | norm | neg | 250 |
| B-POST 10 | 5.0 | 25 | neg | 0.15 | norm | neg | norm | neg | 250 |

NORMAL URINE LEVELS:
BILIRUBIN = 2–20 μmoles/L
TOTAL PROTEIN =< 0.14 g/day
SODIUM = 10–300 mmoL/L
POTASSIUM = 1.0–140.0 mmoL/L
CHLORINE = 20–300 mmoL/L
NORMAL SERUM LEVELS:
BILIRUBIN = 2–20 μmoles/L
TOTAL PROTEIN = 60–80 g/L
SODIUM = 135–147 mmol/L
POTASSIUM = 3.5–5.0 mmol/L
CHLORINE = 97–106 mmol/L
PLASMA Hg =< 0.10 g/L
PLASMA glucose = 700–1050 μg/mL

TABLE 9

CLEANING VALIDATION BENCHMARKS FOR PROTEIN (ug/ml) FOUND IN PATIENT-USED ENDOSCOPE FLEXIBLE ENDOSCOPE CHANNELS:

| | PRE-CLEANING: | | POST-CLEANING: | |
|---|---|---|---|---|
| | Average: (ug/ml) | Range: (ug/ml) | Average: (ug/ml) | Range: (ug/ml) |
| Bronchoscope | 50 | 8–437 | 28 | 17–39 |
| Duodenoscope | 168 | 27–441 | 17 | 3–30 |
| Colonoscope | 711 | 4–2218 | 17 | 1–23 |

Chemistrip needs approximately 30 ug/ml to flag as positive, therefore, would be expected to flag positive for the majority of pre-cleaned bronchoscopes, duodenoscopes and colonoscopes, and would be expected to flag negative for the majority of post-cleaned flexible endoscopes.

TABLE 10

CLEANING VALIDATION KIT BENCHMARKS FOR HEMOGLOBIN (BLOOD) (ug/ml) IN PATIENT-USED ENDOSCOPE FLEXIBLE ENDOSCOPE CHANNELS:

| | PRE-CLEANING: | | POST-CLEANING: | |
|---|---|---|---|---|
| | Average: (ug/ml) | Range: (ug/ml) | Average: (ug/ml) | Range: (ug/ml) |
| Bronchoscope | 61 | 0–390 | 10 | 0–20 |
| Duodenoscope | 30 | 0–190 | 0 | 0–0 |
| Colonoscope | 124 | 0–670 | 0 | 0–0 |

Chemistrip needs approximately 10 ug/ml to flag as positive therefore, would be expected to flag positive for the majority of pre-cleaned bronchoscopes, duodenoscopes and colonoscopes, and would be expected to flag negative for the majority of post-cleaned flexible endoscopes.

I claim:

1. An artificial test soil comprising: base medium, serum, blood and endotoxin.

2. An artificial test soil according to claim 1 comprising up to 20% v/v serum; up to 10% v/v blood and up to 2,000,000 EU/ml endotoxin.

3. An artificial test soil according to claim 1 wherein the base medium is Roswell Park Memorial Institute medium (RPMI).

4. An artificial test soil according to claim 1 wherein the serum is calf serum.

5. An artificial test soil according to claim 1 wherein the endotoxin is derived from lipopolysaccharide (LPS).

6. An artificial test soil according to claim 1 further comprising bilirubin.

7. An artificial test soil according to claim 6 wherein the bilirubin is present in an amount of about 1,000 nmoles/ml.

8. An artificial test soil according to claim 7 where the bilirubin is derived from oxgall bile.

9. An artificial test soil according to claim 1 further comprising mucin or carbohydrate.

10. An artificial test soil according to claim 9 wherein the mucin or carbohydrate is present in the amount of about 10,000 μg/ml.

11. An artificial test soil according to claim 10 wherein the carbohydrate is derived from L-Glutamine.

12. An artificial test soil according to claim 1 that mimics a gastrointestinal site comprising:
RPMI 1640
LPS
Calf Serum
Bovine Oxgall
Sterile Sheep Blood
Sodium Bicarbonate
Sodium-Pyvuvate and
L-Glutamine.

13. An artificial test soil according to claim 1 that mimics soil related to a lung site comprising:
RPMI 1640
LPS
Calf Serum Sterile Sheep Blood
Sodium Bicarbonate
Sodium-Pyvuvate and
L-Glutamine.

14. A test kit comprising an artificial test soil according to claim 1 and an indicator that determines the presence of a contaminant.

15. A test kit according to claim 14 wherein an indicator can detect the presence of more than one contaminant.

16. A kit according to claim 15 wherein the indicator can detect the presence of blood, protein and leukocyte esterase.

17. A method of evaluating a reprocessing method on a device comprising:
(a) applying an artificial test soil (ATS) comprising base medium, serum, blood and endotoxin to the device;
(b) subjecting the device to the reprocessing method to be evaluated; and
(c) determining the presence or absence of at least one contaminant on the device.

18. A method according to claim 17 wherein the contaminant is selected from the group consisting of blood, protein and leukocyte esterase.

19. A method according to claim 17 wherein the device is a medical device.

20. A method according to claim 19 wherein the medical device is selected from the group consisting of flexible endoscopes, narrowed lumened accessory devices and balloon catheters.

21. A method of determining whether a reprocessing method can kill a microorganism on a device comprising:
(a) inoculating an artificial test soil (ATS) with a microorganism wherein the ATS comprises base medium, serum, blood or hemoglobin and endotoxin;
(b) applying the inoculated ATS to the device;
(c) subjecting the device to the reprocessing method to be evaluated; and
(d) determining the presence or absence of the microorganism on the device, wherein the absence of the microorganism on the device indicates that reprocessing method can kill the microorganism.

* * * * *